United States Patent
Song et al.

(10) Patent No.: US 7,651,841 B2
(45) Date of Patent: Jan. 26, 2010

(54) POLYELECTROLYTIC INTERNAL CALIBRATION SYSTEM OF A FLOW-THROUGH ASSAY

(75) Inventors: Xuedong Song, Roswell, GA (US); Ning Wei, Roswell, GA (US); Curt Sayre, Atlanta, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 605 days.

(21) Appl. No.: 10/132,421

(22) Filed: Apr. 25, 2002

(65) Prior Publication Data

US 2003/0124739 A1      Jul. 3, 2003

Related U.S. Application Data

(63) Continuation-in-part of application No. 10/035,014, filed on Dec. 24, 2001, now abandoned.

(51) Int. Cl.
| | |
|---|---|
| *G01N 33/53* | (2006.01) |
| *C12M 1/34* | (2006.01) |
| *C12M 3/00* | (2006.01) |
| *G01N 33/00* | (2006.01) |
| *C12Q 1/50* | (2006.01) |
| *G01N 33/543* | (2006.01) |
| *G01N 33/566* | (2006.01) |
| *G01N 21/77* | (2006.01) |
| *G01N 33/546* | (2006.01) |
| *G01N 31/22* | (2006.01) |

(52) U.S. Cl. ............... 435/7.1; 435/6; 435/287.1; 435/287.2; 435/7.92; 435/17; 436/518; 436/169; 436/501; 436/533; 436/534; 422/56; 422/57

(58) Field of Classification Search ............ 435/6, 435/287.2, 7.1, 287.1, 7.92, 17, 607.4; 436/518, 436/169, 501, 533, 534; 422/56, 57
See application file for complete search history.

(56) References Cited

U.S. PATENT DOCUMENTS 164,659 A      5/1875      Reckhow et al.

(Continued)

FOREIGN PATENT DOCUMENTS

EP      0073593 A1      3/1983

(Continued)

OTHER PUBLICATIONS

Ning Wei et al., U.S. Appl. No. 10/132,673, filed Apr. 25, 2002, Internal Calibration System for Flow-Through Assays.

(Continued)

*Primary Examiner*—Mark L Shibuya
*Assistant Examiner*—Jacqueline Diramio
(74) *Attorney, Agent, or Firm*—Dority & Manning, P.A.

(57) ABSTRACT

A flow-through assay for detecting the quantity of an analyte residing in a test sample is provided. The flow-through assay contains a porous membrane that is in fluid communication with probe conjugates that contain a specific binding member and a detectable probe. The porous membrane also defines a detection zone and a calibration zone. The calibration zone contains a polyelectrolyte substantially non-diffusively immobilized on the porous membrane. The polyelectrolyte is capable of generating a detectable calibration signal that can be readily compared (visually, quantitatively, and the like) to a detection signal to determine the amount of analyte in the test sample.

15 Claims, 9 Drawing Sheets

U.S. PATENT DOCUMENTS

| | | |
|---|---|---|
| 3,700,623 A | 10/1972 | Keim |
| 3,772,076 A | 11/1973 | Keim |
| 4,094,647 A | 6/1978 | Deutsch et al. |
| 4,110,529 A | 8/1978 | Stoy |
| 4,115,535 A | 9/1978 | Giaever |
| 4,168,146 A | 9/1979 | Grubb et al. |
| RE30,267 E | 5/1980 | Bruschi |
| 4,210,723 A | 7/1980 | Dorman et al. |
| 4,235,601 A | 11/1980 | Deutsch et al. |
| 4,275,149 A | 6/1981 | Litman et al. |
| 4,312,228 A | 1/1982 | Wohltjen |
| 4,361,537 A | 11/1982 | Deutsch et al. |
| 4,363,874 A | 12/1982 | Greenquist |
| 4,366,241 A | 12/1982 | Tom et al. |
| 4,374,925 A | 2/1983 | Litman |
| 4,385,126 A | 5/1983 | Chen et al. |
| 4,426,451 A | 1/1984 | Columbus |
| 4,427,836 A | 1/1984 | Kowalski et al. |
| 4,435,504 A | 3/1984 | Zuk et al. |
| 4,441,373 A | 4/1984 | White |
| 4,442,204 A | 4/1984 | Greenquist et al. |
| 4,444,592 A | 4/1984 | Ludwig |
| 4,477,635 A | 10/1984 | Mitra |
| 4,480,042 A | 10/1984 | Craig et al. |
| 4,533,499 A | 8/1985 | Clark et al. |
| 4,533,629 A | 8/1985 | Litman et al. |
| 4,534,356 A | 8/1985 | Papadakis |
| 4,537,657 A | 8/1985 | Keim |
| 4,537,861 A | 8/1985 | Elings et al. |
| 4,540,659 A | 9/1985 | Litman et al. |
| 4,552,458 A | 11/1985 | Lowne |
| 4,561,286 A | 12/1985 | Sekler et al. |
| 4,562,157 A | 12/1985 | Lowe et al. |
| 4,595,661 A | 6/1986 | Cragle et al. |
| 4,596,697 A | 6/1986 | Ballato |
| 4,614,723 A | 9/1986 | Schmidt et al. |
| 4,632,559 A | 12/1986 | Brunsting |
| 4,661,235 A | 4/1987 | Krull et al. |
| 4,698,262 A | 10/1987 | Schwartz et al. |
| 4,703,017 A | 10/1987 | Campbell et al. |
| 4,722,889 A | 2/1988 | Lee et al. |
| 4,727,019 A | 2/1988 | Valkirs et al. |
| 4,731,337 A | 3/1988 | Luotola et al. |
| 4,742,011 A | 5/1988 | Blake et al. |
| 4,743,542 A | 5/1988 | Graham, Jr. et al. |
| 4,743,560 A | 5/1988 | Campbell et al. |
| 4,776,944 A | 10/1988 | Janata et al. |
| 4,806,312 A | 2/1989 | Greenquist |
| 4,835,099 A | 5/1989 | Mize et al. |
| 4,837,168 A | 6/1989 | de Jaeger et al. |
| 4,842,783 A | 6/1989 | Blaylock |
| 4,843,000 A | 6/1989 | Litman et al. |
| 4,843,021 A | 6/1989 | Noguchi et al. |
| 4,844,613 A | 7/1989 | Batchelder et al. |
| 4,849,338 A | 7/1989 | Litman et al. |
| 4,855,240 A | 8/1989 | Rosenstein et al. |
| 4,857,453 A | 8/1989 | Ullman et al. |
| 4,867,908 A | 9/1989 | Recktenwald et al. |
| 4,877,586 A | 10/1989 | Devaney, Jr. et al. |
| 4,877,747 A | 10/1989 | Stewart |
| 4,889,816 A | 12/1989 | Davis et al. |
| 4,895,017 A | 1/1990 | Pyke et al. |
| 4,904,583 A | 2/1990 | Mapes et al. |
| 4,916,056 A | 4/1990 | Brown, III et al. |
| 4,917,503 A | 4/1990 | Bhattacharjee |
| 4,920,046 A | 4/1990 | McFarland et al. |
| 4,940,734 A | 7/1990 | Ley et al. |
| 4,954,435 A | 9/1990 | Krauth |
| 4,956,302 A | 9/1990 | Gordon et al. |
| 4,963,498 A | 10/1990 | Hillman et al. |
| 4,973,670 A | 11/1990 | McDonald et al. |
| 4,978,625 A | 12/1990 | Wagner et al. |
| 4,980,298 A | 12/1990 | Blake et al. |
| 4,992,385 A | 2/1991 | Godfrey |
| 5,003,178 A | 3/1991 | Livesay |
| 5,023,053 A | 6/1991 | Finlan |
| 5,026,653 A | 6/1991 | Lee et al. |
| 5,035,863 A | 7/1991 | Finlan et al. |
| 5,055,265 A | 10/1991 | Finlan |
| 5,063,081 A | 11/1991 | Cozzette et al. |
| 5,064,619 A | 11/1991 | Finlan |
| 5,073,340 A | 12/1991 | Covington et al. |
| 5,075,077 A | 12/1991 | Durley, III et al. |
| 5,075,078 A | 12/1991 | Osikowicz et al. |
| 5,076,094 A | 12/1991 | Frye et al. |
| 5,096,671 A | 3/1992 | Kane et al. |
| 5,114,676 A | 5/1992 | Leiner et al. |
| 5,120,643 A | 6/1992 | Ching et al. |
| 5,120,662 A | 6/1992 | Chan et al. |
| 5,124,254 A | 6/1992 | Hewlins et al. |
| 5,134,057 A | 7/1992 | Kuypers et al. |
| 5,137,609 A | 8/1992 | Manian et al. |
| 5,143,854 A | 9/1992 | Pirrung et al. |
| 5,145,784 A | 9/1992 | Cox et al. |
| 5,149,622 A | 9/1992 | Brown et al. |
| 5,152,758 A | 10/1992 | Kaetsu et al. |
| 5,156,953 A | 10/1992 | Litman et al. |
| 5,166,079 A | 11/1992 | Blackwood et al. |
| 5,182,135 A | 1/1993 | Giesecke et al. |
| 5,185,127 A | 2/1993 | Vonk |
| 5,196,350 A | 3/1993 | Backman et al. |
| 5,200,084 A | 4/1993 | Liberti et al. |
| 5,208,143 A | 5/1993 | Henderson et al. |
| 5,208,535 A | 5/1993 | Nakayama et al. |
| 5,221,454 A | 6/1993 | Manian et al. |
| 5,225,935 A | 7/1993 | Watanabe et al. |
| 5,234,813 A | 8/1993 | McGeehan et al. |
| 5,235,238 A | 8/1993 | Nomura et al. |
| 5,238,815 A | 8/1993 | Higo et al. |
| 5,242,828 A | 9/1993 | Bergström et al. |
| 5,252,459 A | 10/1993 | Tarcha et al. |
| 5,262,299 A | 11/1993 | Evangelista et al. |
| 5,268,306 A | 12/1993 | Berger et al. |
| 5,275,785 A | 1/1994 | May et al. |
| 5,314,923 A | 5/1994 | Cooke et al. |
| 5,316,727 A | 5/1994 | Suzuki et al. |
| 5,320,944 A | 6/1994 | Okada et al. |
| 5,321,492 A | 6/1994 | Detwiler et al. |
| 5,327,225 A | 7/1994 | Bender et al. |
| 5,330,898 A | 7/1994 | Bar-Or et al. |
| 5,342,759 A | 8/1994 | Litman et al. |
| 5,352,582 A | 10/1994 | Lichtenwalter et al. |
| 5,356,782 A | 10/1994 | Moorman et al. |
| 5,358,852 A | 10/1994 | Wu |
| 5,369,717 A | 11/1994 | Attridge |
| 5,374,531 A | 12/1994 | Jensen |
| 5,374,563 A | 12/1994 | Maule |
| 5,376,255 A | 12/1994 | Gumbrecht et al. |
| 5,387,503 A | 2/1995 | Selmer et al. |
| 5,395,754 A | 3/1995 | Lambotte et al. |
| 5,415,842 A | 5/1995 | Maule |
| 5,418,136 A | 5/1995 | Miller et al. |
| 5,424,219 A | 6/1995 | Jirikowski |
| 5,428,690 A | 6/1995 | Bacus et al. |
| 5,432,057 A | 7/1995 | Litman et al. |
| 5,436,161 A | 7/1995 | Bergström et al. |
| 5,445,971 A | 8/1995 | Rohr |
| 5,451,683 A | 9/1995 | Barrett et al. |
| 5,455,475 A | 10/1995 | Josse et al. |
| 5,464,741 A | 11/1995 | Hendrix |
| 5,466,574 A | 11/1995 | Liberti et al. |
| 5,467,778 A | 11/1995 | Catt et al. |
| 5,468,606 A | 11/1995 | Bogart et al. |
| 5,482,830 A | 1/1996 | Bogart et al. |

| Patent | | Date | Inventor |
|---|---|---|---|
| 5,482,867 | A | 1/1996 | Barrett et al. |
| 5,484,867 | A | 1/1996 | Lichtenham et al. |
| 5,489,678 | A | 2/1996 | Fodor et al. |
| 5,489,988 | A | 2/1996 | Ackley et al. |
| 5,492,840 | A | 2/1996 | Malmqvist et al. |
| 5,500,350 | A | 3/1996 | Baker et al. |
| 5,504,013 | A | 4/1996 | Senior |
| 5,508,171 | A | 4/1996 | Walling et al. |
| 5,510,481 | A | 4/1996 | Bednarski et al. |
| 5,512,131 | A | 4/1996 | Kumar et al. |
| 5,514,559 | A | 5/1996 | Markert-Hahn et al. |
| 5,514,785 | A | 5/1996 | Van Ness et al. |
| 5,516,635 | A | 5/1996 | Ekins et al. |
| 5,518,689 | A | 5/1996 | Dosmann et al. |
| 5,518,883 | A | 5/1996 | Soini |
| 5,527,711 | A | 6/1996 | Tom-Moy et al. |
| 5,534,132 | A | 7/1996 | Vreeke et al. |
| 5,554,541 | A | 9/1996 | Malmqvist et al. |
| 5,569,608 | A | 10/1996 | Sommer |
| 5,571,684 | A | 11/1996 | Lawrence et al. |
| 5,573,909 | A | 11/1996 | Singer et al. |
| 5,573,919 | A | 11/1996 | Kearns et al. |
| 5,585,279 | A | 12/1996 | Davidson |
| 5,589,401 | A | 12/1996 | Hansen et al. |
| 5,591,581 | A | 1/1997 | Massey et al. |
| 5,591,645 | A | 1/1997 | Rosenstein |
| 5,596,414 | A | 1/1997 | Tyler |
| 5,599,668 | A | 2/1997 | Stimpson et al. |
| 5,602,040 | A | 2/1997 | May et al. |
| 5,610,077 | A | 3/1997 | Davis et al. |
| 5,618,732 | A | 4/1997 | Pease et al. |
| 5,618,888 | A | 4/1997 | Choi et al. |
| 5,620,850 | A | 4/1997 | Bamdad et al. |
| 5,622,871 | A | 4/1997 | May et al. |
| 5,637,509 | A | 6/1997 | Hemmilä et al. |
| 5,647,994 | A | 7/1997 | Tuunanen et al. |
| 5,656,503 | A | 8/1997 | May et al. |
| 5,658,443 | A | 8/1997 | Yamamoto et al. |
| 5,663,213 | A | 9/1997 | Jones et al. |
| 5,670,381 | A | 9/1997 | Jou et al. |
| 5,672,256 | A | 9/1997 | Yee |
| 5,700,636 | A | 12/1997 | Sheiness et al. |
| 5,714,389 | A | 2/1998 | Charlton et al. |
| 5,726,064 | A | 3/1998 | Robinson et al. |
| 5,731,147 | A | 3/1998 | Bard et al. |
| 5,736,188 | A | 4/1998 | Alcock et al. |
| 5,753,517 | A | 5/1998 | Brooks et al. |
| 5,770,416 | A | 6/1998 | Lihme et al. |
| 5,780,308 | A | 7/1998 | Ching et al. |
| 5,788,863 | A | 8/1998 | Milunic |
| 5,795,470 | A | 8/1998 | Wang et al. |
| 5,795,543 | A | 8/1998 | Poto et al. |
| 5,798,273 | A | 8/1998 | Shuler et al. |
| 5,811,526 | A | 9/1998 | Davidson |
| 5,827,748 | A | 10/1998 | Golden |
| 5,834,226 | A | 11/1998 | Maupin |
| 5,837,429 | A | 11/1998 | Nohr et al. |
| 5,837,546 | A | 11/1998 | Allen et al. |
| 5,837,547 | A | 11/1998 | Schwartz |
| 5,843,692 | A | 12/1998 | Phillips et al. |
| 5,852,229 | A | 12/1998 | Josse et al. |
| 5,876,944 | A | 3/1999 | Kuo |
| 5,885,527 | A | 3/1999 | Buechler |
| 5,906,921 | A | 5/1999 | Ikeda et al. |
| 5,910,447 | A | 6/1999 | Lawrence et al. |
| 5,910,940 | A | 6/1999 | Guerra |
| 5,922,537 | A | 7/1999 | Ewart et al. |
| 5,922,550 | A | 7/1999 | Everhart et al. |
| 5,945,281 | A | 8/1999 | Prabhu |
| 5,951,492 | A | 9/1999 | Douglas et al. |
| 5,962,995 | A | 10/1999 | Avnery |
| 5,968,839 | A | 10/1999 | Blatt et al. |
| 5,985,432 | A * | 11/1999 | Wang et al. ............... 428/304.4 |
| 5,989,924 | A | 11/1999 | Root et al. |
| 5,989,926 | A | 11/1999 | Badley et al. |
| 5,998,221 | A | 12/1999 | Malick et al. |
| 6,001,658 | A * | 12/1999 | Fredrickson ................ 436/514 |
| 6,004,530 | A | 12/1999 | Sagner et al. |
| 6,020,047 | A | 2/2000 | Everhart |
| 6,027,904 | A | 2/2000 | Devine et al. |
| 6,027,943 | A * | 2/2000 | Kang et al. ................. 436/518 |
| 6,027,944 | A | 2/2000 | Robinson et al. |
| 6,030,792 | A | 2/2000 | Otterness et al. |
| 6,030,840 | A | 2/2000 | Mullinax et al. |
| 6,033,574 | A | 3/2000 | Siddiqi |
| 6,048,623 | A | 4/2000 | Everhart et al. |
| 6,057,165 | A | 5/2000 | Mansour |
| 6,060,256 | A | 5/2000 | Everhart et al. |
| 6,077,669 | A | 6/2000 | Little et al. |
| 6,080,391 | A | 6/2000 | Tsuchiya et al. |
| 6,084,683 | A | 7/2000 | Bruno et al. |
| 6,087,184 | A | 7/2000 | Magginetti et al. |
| 6,099,484 | A | 8/2000 | Douglas et al. |
| 6,103,537 | A | 8/2000 | Ullman et al. |
| 6,117,090 | A | 9/2000 | Caillouette |
| 6,130,100 | A | 10/2000 | Jobling et al. |
| 6,133,048 | A | 10/2000 | Penfold et al. |
| 6,136,549 | A | 10/2000 | Feistel |
| 6,136,611 | A | 10/2000 | Saaski et al. |
| 6,139,961 | A | 10/2000 | Blankenship et al. |
| 6,151,110 | A | 11/2000 | Markart |
| 6,156,271 | A | 12/2000 | May |
| 6,165,798 | A | 12/2000 | Brooks |
| 6,171,646 | B1 | 1/2001 | Hirai et al. |
| 6,171,780 | B1 | 1/2001 | Pham et al. |
| 6,171,870 | B1 | 1/2001 | Freitag |
| 6,177,281 | B1 | 1/2001 | Manita |
| 6,180,288 | B1 | 1/2001 | Everhart et al. |
| 6,183,972 | B1 | 2/2001 | Kuo et al. |
| 6,184,042 | B1 | 2/2001 | Neumann et al. |
| 6,187,269 | B1 | 2/2001 | Lancesseru et al. |
| 6,194,220 | B1 | 2/2001 | Malick et al. |
| 6,200,820 | B1 | 3/2001 | Hansen et al. |
| 6,221,238 | B1 | 4/2001 | Grundig et al. |
| 6,221,579 | B1 | 4/2001 | Everhart et al. |
| 6,234,974 | B1 | 5/2001 | Catt et al. |
| 6,235,241 | B1 | 5/2001 | Catt et al. |
| 6,235,471 | B1 | 5/2001 | Knapp et al. |
| 6,235,491 | B1 | 5/2001 | Connolly |
| 6,241,863 | B1 | 6/2001 | Monbouquette |
| 6,242,268 | B1 | 6/2001 | Wieder et al. |
| 6,255,066 | B1 | 7/2001 | Louderback |
| 6,261,779 | B1 | 7/2001 | Barbera-Guillem et al. |
| 6,268,222 | B1 | 7/2001 | Chandler et al. |
| 6,270,637 | B1 | 8/2001 | Crismore et al. |
| 6,271,040 | B1 | 8/2001 | Buechler |
| 6,274,324 | B1 | 8/2001 | Davis et al. |
| 6,281,006 | B1 | 8/2001 | Heller et al. |
| 6,284,472 | B1 | 9/2001 | Wei et al. |
| 6,287,783 | B1 | 9/2001 | Maynard et al. |
| 6,287,871 | B1 | 9/2001 | Herron et al. |
| 6,294,391 | B1 | 9/2001 | Badley et al. |
| 6,294,392 | B1 | 9/2001 | Kuhr et al. |
| 6,306,665 | B1 | 10/2001 | Buck et al. |
| D450,854 | S | 11/2001 | Lipman et al. |
| 6,331,438 | B1 | 12/2001 | Aylott et al. |
| 6,348,186 | B1 | 2/2002 | Sutton et al. |
| 6,352,862 | B1 | 3/2002 | Davis et al. |
| 6,362,011 | B1 | 3/2002 | Massey et al. |
| 6,368,873 | B1 | 4/2002 | Chang et al. |
| 6,368,875 | B1 | 4/2002 | Geisberg |
| 6,387,707 | B1 | 5/2002 | Seul et al. |
| 6,391,558 | B1 | 5/2002 | Henkens et al. |
| 6,399,295 | B1 | 6/2002 | Kaylor et al. |
| 6,399,397 | B1 | 6/2002 | Zarling et al. |
| 6,399,398 | B1 | 6/2002 | Cunningham et al. |

| | | | | | | |
|---|---|---|---|---|---|---|
| 6,407,492 B1 | 6/2002 | Avnery et al. | | EP | 1221616 A1 | 7/2002 |
| 6,411,439 B2 | 6/2002 | Nishikawa | | EP | 1255111 A1 | 11/2002 |
| 6,413,410 B1 | 7/2002 | Hodges et al. | | GB | 2273772 A | 6/1994 |
| 6,436,651 B1 | 8/2002 | Everhart et al. | | WO | WO 8804777 A1 | 6/1988 |
| 6,436,722 B1 | 8/2002 | Clark et al. | | WO | WO 9005305 A1 | 5/1990 |
| 6,444,423 B1 | 9/2002 | Meade et al. | | WO | WO 9105999 A2 | 5/1991 |
| 6,448,091 B1 | 9/2002 | Massey et al. | | WO | WO 9221769 | 12/1992 |
| 6,451,607 B1 | 9/2002 | Lawrence et al. | | WO | WO 9221770 | 12/1992 |
| 6,455,861 B1 | 9/2002 | Hoyt | | WO | WO 9221975 | 12/1992 |
| 6,461,496 B1 | 10/2002 | Feldman et al. | | WO | WO 9301308 A1 | 1/1993 |
| 6,468,741 B1 | 10/2002 | Massey et al. | | WO | WO 9319370 A1 | 3/1993 |
| 6,472,226 B1 | 10/2002 | Barradine et al. | | WO | WO 9406012 | 3/1994 |
| 6,479,146 B1 | 11/2002 | Caruso et al. | | WO | WO 9413835 A1 | 6/1994 |
| 6,509,085 B1 | 1/2003 | Kennedy | | WO | WO 9415193 A1 | 7/1994 |
| 6,509,196 B1 | 1/2003 | Brooks et al. | | WO | WO 9709620 | 3/1997 |
| 6,511,814 B1 | 1/2003 | Carpenter | | WO | WO 9709620 A1 | 3/1997 |
| 6,524,864 B2 | 2/2003 | Fernandez de Castro | | WO | WO 9737222 A1 | 10/1997 |
| 6,556,299 B1 | 4/2003 | Rushbrooke et al. | | WO | WO 9810334 A1 | 3/1998 |
| 6,566,508 B2 | 5/2003 | Bentsen et al. | | WO | WO 9815831 A1 | 4/1998 |
| 6,573,040 B2 | 6/2003 | Everhart et al. | | WO | WO 9827417 A1 | 6/1998 |
| 6,579,673 B2 | 6/2003 | McGrath et al. | | WO | WO 9843086 A1 | 10/1998 |
| 6,582,930 B1 | 6/2003 | Ponomarev et al. | | WO | WO 9910742 A1 | 3/1999 |
| 6,585,939 B1 | 7/2003 | Dapprich | | WO | WO 9930131 A1 | 6/1999 |
| 6,613,583 B1 | 9/2003 | Richter et al. | | WO | WO 9936777 | 7/1999 |
| 6,617,488 B1 | 9/2003 | Springer et al. | | WO | WO 9964864 A1 | 12/1999 |
| 6,627,459 B1 | 9/2003 | Tung et al. | | WO | WO 0019199 A1 | 4/2000 |
| 6,653,149 B1 | 11/2003 | Tung et al. | | WO | WO 0023805 A1 | 4/2000 |
| 6,669,908 B2 | 12/2003 | Weyker et al. | | WO | WO 0034781 A1 | 6/2000 |
| 6,670,115 B1 | 12/2003 | Zhang | | WO | WO 0036416 A1 | 6/2000 |
| RE38,430 E | 2/2004 | Rosenstein | | WO | WO 0046839 A2 | 8/2000 |
| 6,720,007 B2 | 4/2004 | Walt et al. | | WO | WO 0046839 A3 | 8/2000 |
| 6,787,368 B1 | 9/2004 | Wong et al. | | WO | WO 0047983 A1 | 8/2000 |
| 6,815,218 B1 | 11/2004 | Jacobson et al. | | WO | WO 0050891 A1 | 8/2000 |
| 6,916,666 B1* | 7/2005 | Mendel-Hartvig et al. .. 436/518 | | WO | WO 0078917 A1 | 12/2000 |
| 6,951,631 B1 | 10/2005 | Catt et al. | | WO | WO 0129559 A1 | 4/2001 |
| 7,044,919 B1 | 5/2006 | Catt et al. | | WO | WO 0138873 A2 | 5/2001 |
| 7,052,831 B2 | 5/2006 | Fletcher et al. | | WO | WO 0150129 A2 | 7/2001 |
| 2001/0055776 A1 | 12/2001 | Greenwalt | | WO | WO 0150129 A3 | 7/2001 |
| 2002/0042149 A1 | 4/2002 | Butlin et al. | | WO | WO 0163299 A1 | 8/2001 |
| 2002/0045273 A1 | 4/2002 | Butlin et al. | | WO | WO 0171344 A2 | 9/2001 |
| 2002/0070128 A1 | 6/2002 | Beckmann | | WO | WO 0198765 A1 | 12/2001 |
| 2002/0132282 A1* | 9/2002 | Ouyang et al. ................. 435/25 | | WO | WO 0198785 A2 | 12/2001 |
| 2002/0146754 A1 | 10/2002 | Kitawaki et al. | | WO | WO 02077646 A1 | 10/2002 |
| 2002/0164659 A1 | 11/2002 | Rao et al. | | WO | WO 03005013 A1 | 1/2003 |
| 2003/0017615 A1 | 1/2003 | Sidwell et al. | | WO | WO 03008971 A2 | 1/2003 |
| 2003/0175517 A1* | 9/2003 | Voigt et al. ............... 428/402.2 | | WO | WO 03008971 A3 | 1/2003 |
| 2003/0178309 A1 | 9/2003 | Huang et al. | | WO | WO 03058246 A1 | 7/2003 |
| 2004/0014073 A1 | 1/2004 | Trau et al. | | WO | WO 2004034056 A2 | 4/2004 |
| 2004/0121334 A1* | 6/2004 | Wei et al. ........................ 435/6 | | WO | WO 2004034056 A3 | 4/2004 |
| 2004/0152963 A1* | 8/2004 | March ........................ 600/319 | | | | |
| 2005/0214827 A1* | 9/2005 | Virtanen ........................ 435/6 | | | | |
| 2006/0008921 A1* | 1/2006 | Daniels et al. ............. 436/514 | | | | |

FOREIGN PATENT DOCUMENTS

| | | |
|---|---|---|
| EP | 0205698 A1 | 12/1986 |
| EP | 0420053 | 4/1991 |
| EP | 0462376 B1 | 12/1991 |
| EP | 0469377 A2 | 2/1992 |
| EP | 0539034 B1 | 4/1993 |
| EP | 0539035 A2 | 4/1993 |
| EP | 0617285 A2 | 9/1994 |
| EP | 0617285 A3 | 9/1994 |
| EP | 0657737 A2 | 6/1995 |
| EP | 0657737 A3 | 6/1995 |
| EP | 0703454 A1 | 3/1996 |
| EP | 0437287 | 7/1996 |
| EP | 0724156 A1 | 7/1996 |
| EP | 0745843 A2 | 12/1996 |
| EP | 0745843 A3 | 12/1996 |
| EP | 0833159 A2 | 4/1998 |
| EP | 0859230 A1 | 8/1998 |
| EP | 0898169 B1 | 2/1999 |

OTHER PUBLICATIONS

Canterero et al. "The Absorption Characteristics of Proteins for Polystyrene and Their Significance in Solid Phase Immunoassyas," Analytical Biochemistry 105, 375-382 (1980).

EPO Search Report, Apr. 11, 2003.

*Magnetic Microparticles*, Polysciences, Inc. Technical Data Sheet 438, 2 pages, Publication Undated.

*Flow-Based Microimmunoassay*, Analytical Chemistry, vol. 73, No. 24, Mark A. Hayes, Nolan A. Polson, Allison, N. Phayre, and Antonia A. Garcia, pp. 5896-5902, Dec. 15, 2001.

Article—*How to Build a Spectrofluorometer*, Spex Fluorolog 3, Horiba Group, pp. 1-14.

Article—*Principle and Applications of Size-Exclusion Chromatography*, Impact Analytical, pp. 1-3.

Article—*A New Tetradentate β-Diketonate-Europium Chelate That Can Be Covalently Bound to Proteins for Time-Resolved Fluoroimmunoassay*, Jingli Yuan and Kazuko Matsumoto, Analytical Chemistry, vol. 70, No. 3, Feb. 1, 1998, pp. 596-601.

Article—*One-step all-in-one dry reagent immunoassays with fluorescent europium chelate label and time-resolved fluorometry*, Timo Lövgren, Liisa Meriö, Katja Mitrunen, Maija-Liisa Mäkinen, Minna Mäkelä, Kaj Blomberg, Tom Palenius, and Kim Pettersson, Clinical Chemistry 42:8, 1996, pp. 1196-1201.

Article—*Europium Chelate Labels in Time-Resolved Fluorescence Immunoassays and DNA Hybridization Assays*, Eleftherios P. Diamandis and Theodore K. Christopoulos, Analytical Chemistry, vol. 62, No. 22, Nov. 15, 1990, pp. 1149-1157.

Article—*Polymer Based Lanthanide Luminescent Sensors for the Detection of Nerve Agents*, Amanda L. Jenkins, O. Manuel Uy, and George M. Murray, Analytical Communications, vol. 34, Aug. 1997, pp. 221-224.

Article—*Separation-Free Sandwich Enzyme Immunoassays Using Microporous Gold Electrodes and Self-Assembled Monolayer/Immobilized Capture Antibodies*, Chuanming Duan and Mark E. Meyerhoff, Analytical Chemistry, vol. 66, No. 9, May 1, 1994, pp. 1369-1377.

Article—*Hydrogen Peroxide and β-Nicotinamide Adenine Dinucleotide Sensing Amperometric Electrodes Based on Electrical Connection of Horseradish Peroxidase Redox Centers to Electrodes Through a Three-Dimensional Electron Relaying Polymer Network*, Mark Vreeke, Ruben Maidan, and Adam Heller, Analytical Chemistry, vol. 64, No. 24, Dec. 15, 1992, pp. 3084-3090.

Article—*A Thermostable Hydrogen Peroxide Sensor Based on "Wiring" of Soybean Peroxidase*, Mark S. Vreeke, Khin Tsun Yong, and Adam Heller, Analytical Chemistry, vol. 67, No. 23, Dec. 1, 1995, pp. 4247-4249.

Article—*Heterogeneous Enzyme Immunoassay of Alpha-Fetoprotein in Maternal Serum by Flow-Injection Amperometric Detection of 4-Aminophenol*, Yan Xu, H. Brian Haisall, and William R. Heineman, Clinical Chemistry, vol. 36, No. 11, 1990, pp. 1941-1944.

Article—*A Fully Active Monolayer Enzyme Electrode Derivatized by Antigen-Antibody Attachment*, Christian Bourdillon, Christopher Demaille, Jean Gueris, Jacques Moiroux, and Jean-Michel Savéant, J. Am. Chem. Soc., vol. 115, No. 26, 1993, pp. 12264-12269.

Article—*Production of Hollow Microspheres from Nanostructured Composite Particles*, Frank Caruso, Rachel A. Caruso, and Helmuth MöhwaldChem, Mater., vol. 11, No. 11, 1999, pp. 3309-3314.

Article—*Hollow latex particles: synthesis and applications*, Charles J. McDonald and Michael J. Devon, Advances in Colloid and Interface Science, Vo. 99, 2002, pp. 181-213.

Article—*Prediction of Segregation to Alloy Surfaces from Bulk Phase Diagrams*, J. J. Burton and E. S. Machlin, Physical Review Letters, vol. 37, No. 21, Nov. 22, 1976, pp. 1433-1436.

Article—*Orientation dependence of surface segregation in a dilute Ni-Au alloy*, W. C. Johnson, N. G. Chavka, R. Ku, J. L. Bomback, and P. P. Wynblatt, J. Vac. Sci. Technol. vol. 15, No. 2, Mar./Apr. 1978, pp. 467-469.

Article—*Volume Phase Transition of N-Alkylacrylamide Gels*, S. Saito, M. Konno, and H. Inomata, Advances in Polymer Science, vol. 109, 1992, pp. 207-232.

Article—*Molecular Design Temperature-Responsive Polymers as Intelligent Materials*, Teruo Okano, Advances in Polymer Science, pp. 179-197.

Article—*Molecular Gradients of w-Substituted Alkanethiols on Gold: Preparation and Characterization*, Bo Liedberg and Pentti Tengvall, Langmuir, vol. 11, No. 10, 1995, pp. 3821-3827.

Article—*Acoustic Plate Waves for Measurements of Electrical Properties of Liquids*, U. R. Kelkar, F. Josse, D. T. Haworth, and Z. A. Shana, Micromechanical Journal, vol. 43, 1991, pp. 155-164.

Article—*Analysis of electrical equivalent circuit of quartz crystal resonator loaded with viscous conductive liquids*, Journal of Electroanalytical Chemistry, vol. 379, 1994, pp. 21-33.

Article—*Quartz Crystal Resonators as Sensors in Liquids Using the Acoustoelectric Effect*, Zack A. Shana and Fabian Josse, Analytical Chemistry, vol. 66, No. 13, Jul. 1, 1994, pp. 1955-1964.

Article—*Features of gold having micrometer to centimeter dimensions can be formed through a combination of stamping with an elastomeric stamp and an alkanethiol "ink" followed by chemical etching*, Amit Kumar and George M. Whitesides, Appl. Phys. Lett., vol. 63, No. 14, Oct. 4, 1993, pp. 2002-2004.

Article—*Photolithography of self-assembled monolayers: optimization of protecting groups by an electroanalytical method*, Jamila Jennane, Tanya Boutrous, and Richard Giasson, Can. J. Chem., vol. 74, 1996, pp. 2509-2517.

Article—*Order in Microcontact Printed Self-Assembled Monolayers*, N. B. Larsen, H. Biebuyck, E. Delamarche, and B. Michel, J. Am. Chem. Soc., vol. 119, No. 13, 1997, pp. 3017-3026.

Article—*Intelligent Gels*, Yoshihito Osada and Simon B. Ross-Murphy, Scientific American, May 1993, pp. 82-87.

Article—*Electrical Surface Perturbation of a Piezoelectric Acoustic Plate Mode by a Conductive Liquid Loading*, Fabien Josse, IEEE Transactions on Ultrasonics, Ferroelectrics, and Frequency Control, vol. 39, No. 4, Jul. 1992, pp. 512-518.

Article—*On the use of $ZX\text{-}LiNbO_3$ acoustic plate mode devices as detectors for dilute electrolytes*, F. Josse, Z. A. Shana, D. T. Haworth, and S. Liew, Sensors and Actuators B, vol. 9, 1992, pp. 92-112.

Article—*Probing of strong and weak electrolytes with acoustic wave fields*, R. Dahint, D. Grunze, F. Josse, and J. C. Andle, Sensors and Actuators B, vol. 9, 1992, pp. 155-162.

Article—*Patterned Condensation Figures as Optical Diffraction Gratings*, Amit Kumar and George M. Whitesides, Science, vol. 263, Jan. 7, 1994, pp. 60-62.

Article—*Stimuli-Responsive Poly(N-isopropylacrylamide) Photo- and Chemical-Induced Phase Transitions*, Advances in Polymer Science, pp. 50-65.

Article—*Quantitative Prediction of Surface Segregation*, M. P. Seah, Journal of Catalysts, vol. 57, 1979, pp. 450-457.

Article—*Sensing liquid properties with thickness-shear mode resonators*, S. J. Martin, G. C. Frye, and K. O. Wessendorf, Sensors and Actuators A, vol. 44, 1994, pp. 209-218.

Article—*Direct Observation of Streptavidin Specifically Adsorbed on Biotin-Functionalized Self-Assembled Monolayers with the Scanning Tunneling Microscope*, Lukas Häussling, Bruno Michel, Helmut Ringsdorf, and Heinrich Rohrer, Angew Chem. Int. Ed. Engl., vol. 30, No. 5, 1991, pp. 569-572.

Article—*New Approach To Producing Patterned Biomolecular Assemblies*, Suresh K. Bhatia, James J. Hickman, and Frances S. Ligler, J. Am. Chem. Soc., vol. 114, 1992, pp. 4433-4434.

Article—*Photosensitive Self-Assembled Monolayers on Gold: Photochemistry of Surface-Confined Aryl Azide and Cyclopentadienylmanganese Tricarbonyl*, Eric W. Wollman, Doris Kang, C. Daniel Frisbie, Ivan M. Lorkovic and Mark S. Wrighton, J. Am. Chem. Soc., vol. 116, No. 10, 1994, pp. 4395-4404.

Article—*Generation of electrochemically deposited metal patterns by means of electron beam (nano)lithography of self-assembled monolayer resists*, J. A. M. Sondag-Hethorst, H. R. J. van-Helleputte, and L. G. J. Fokkink, Appl. Phys. Lett., vol. 64, No. 3, Jan. 17, 1994, pp. 285-287.

Article—*Patterned Functionalization of Gold and Single Crystal Silicon via Photochemical Reaction of Surface-Confined Derivatives of $(n^5\text{-}C_5H_5)Mn(CO)_3$*, Doris Kang and Mark S. Wrighton, Langmuir, vol. 7, No. 10, 1991, pp. 2169-2174.

Article—*Photopatterning and Selective Electroless Metallization of Surface-Attached Ligands*, Walter J. Dressick, Charles S. Dulcey, Jacque H. Georger, Jr., and Jeffrey M. Calvert, American Chemical Society, 2 pages.

Article—*Fabrication of Patterned, Electrically Conducting Polypyrrole Using a Self-Assembled Monolayer: A Route to All-Organic Circuits*, Christopher B. Gorman, Hans A. Biebuyck, and George M. Whitesides, American Chemical Society, 2 pages.

Article—*The Use of Self-Assembled Monolayers and a Selective Etch To Generate Patterned Gold Features*, Amit Kumar, Hans A. Biebuyck, Nicholas L. Abbott, and George M. Whitesides, Journal of the American Chemical Society, vol. 114, 1992, 2 pages.

Article—*Patterned Metal Electrodeposition Using an Alkanethiolate Mask*, T. P. Moffat and H. Yang, J. Electrochem. Soc., vol. 142, No. 11, Nov. 1995, pp. L220-L222.

Article—*Biospecific Adsorption of Carbonic Anhydrase to Self-Assembled Monolayers of Alkanethiolates That Present Benzenesulfonamide Groups on Gold*, Milan Mrksich, Jocelyn R. Grunwell, and George M. Whitesides, J. Am. Chem. Soc., vol. 117, No. 48, 1995, pp. 12009-12010.

Article—*Attempts of Mimic Docking Processes of the Immune System: Recognition of Protein Multilayers*, W. Müller, H. Ringsdorf, E. Rump, G. Wildburg, X. Zhang, L. Angermaier, W. Knoll, M. Liley, and J. Spinke, Science, vol. 262, Dec. 10, 1993, pp. 1706-1708.
Article—*Mechanical resonance gas sensors with piezoelectric excitation and detection using PVDF polymer foils*, R. Block, G. Fickler, G. Lindner, H. Müller, and M. Wohnhas, Sensors and Actuators B, 1992, pp. 596-601.
Article—*Application of rod-like polymers with ionophores as Langmuir-Blodgett membranes for Si-based ion sensors*, Sensors and Actuators B, 1992, pp. 211-216.
Article—*Optical Bionsensor Assay (OBA™)*, Y. G. Tsay, C. I. Lin, J. Lee, E. K. Gustafson, R. Appelqvist, P. Magginetti, R. Norton, N. Teng, and D. Charlton, Clinical Chemistry, vol. 37, No. 9, 1991, pp. 1502-1505.
Article—*Responsive Gels: Volume Transitions I*, M. Ilavský, H. Inomata, A. Khokhlove, M. Konno, A. Onuki, S. Saito, M. Shibayama, R.A. Siegel, S. Starodubtzev, T. Tanaka, and V. V. Vasiliveskaya, Advances in Polymer Science, vol. 109, 9 pages.
*The colloidal state*, Introduction to Colloid and Surface Chemistry, $4^{th}$ Ed., 17 pages.
*Nanostructured™ Chemicals: Bridging the Gap Between Fillers, Surface Modifications and Reinforcement*, Joseph D. Lichtenhan, Invited lectures: Functional Tire Fillers 2001, Ft. Lauderdale, FL, Jan. 29-31, 2001, pp. 1-15.
*Working With FluoSpheres® Fluorescent Microspheres*, Properties and Modifications, Production Information from Molecular Probes, Mar. 9, 2001, pp. 1-5.
*FluoSpheres® Fluorescent Microspheres*, Production Information from Molecular Probes, Mar. 13, 2001, pp. 1-6.
*Fluorescent Microsphere Standards for Flow Cytometry and Fluorescence Microscopy* from Molecular Probes, pp. 1-8.
*POSS Polymer Systems* from Hybrid Plastics, 3 pages.
*Factors influencing the formation of hollow ceramic microspheres by water extraction of colloidal droplets*, J. Mater. Res., vol. 10, No. 1, p. 84.
*Dualite® Polymeric Microspheres*, from Pierce & Stevens Corp. a subsidiary of Sovereign Specialty Chemicals, Inc., 2 pages.
*ECCOSPHERES® glass microspheres—hollow glass microspheres* from Emerson & Cuming Composite Materials, Inc., 1 page.
*Dynabeads® Biomagnetic Separation Technology—The Principle* from Dynal Biotech, 2 pages.
*CELQUAT® SC-230M (28-6830)*, Polyquaternium-10, from National Starch & Chemical, 1 page.
*CELQUAT® SC-230M (28-6830)*, CELQUAT® SC-240C and SC-230M, from National Starch & Chemical, 1 page.
National Starch & Chemical, Product Information Celquart® SC-230M, "A Sensory Modifier for Cleansing Systems", 5 pages.
*Making sun exposure safer for everyone* from Rohm and Haas Company (Bristol Complex), 2 pages.
Article—*Fine Structure of Human Immunodeficiency Virus (HIV) and Immunolocalization of Structural Proteins*, Hans R. Gelderblom, Elda H.S. Hausmann, Muhsin Özel, George Pauli, and Meinrad A. Koch, Virology, vol. 156, No. 1, Jan. 1987, pp. 171-176.
8 Photographs of Accu-chek® Blood Glucose Meter.
Pamphlet—The ClearPlan® Easy Fertility Monitor.
Article—*Whole Blood Capcellia CD4/CD8 Immunoassay for Enumeration of CD4+ and CD8+ Peripheral T Lymphocytes*, Dominique Corrière, Jean Pierre Vendrell, Claude Fontaine, Aline Jansen, Jacques Reynes, Isabelle Pagès, Catherine Holzmann, Michel Laprade, and Bernard Pau, Clinical Chemistry, vol. 45, No. 1, 1999, pp. 92-97.
Abstract of Japanese Patent No. JP 8062214., Mar. 8, 1996.
PCT Search Report for PCT/US03/28628, Mar. 18, 2004.
PCT Search Report for PCT/US02/37653, Apr. 7, 2004.
PCT Search Report for PCT/US03/34543, Apr. 6, 2004.
PCT Search Report for PCT/US03/34544, Apr. 20, 2004.
Article—*A conductometral biosensor for biosecurity*, Zarini Muhammad-Tahir and Evangelyn C. Alocilja, Biosensors & Bioelectronics, vol. 18, 2003, pp. 813-819.
Article—*A Disposable Amperometric Sensor Screen Printed on a Nitrocellulose Strip: A Glucose Biosensor Employing Lead Oxide as an Interference-Removing Agent*Gang Cui, San Jin Kim, Sung Hyuk Choi, Hakhyun Nam, and Geun Sig Cha, Analytical Chemistry, vol. 72, No. 8, Apr. 15, 2000, pp. 1925-1929.
Article—*Amine Content of Vaginal Fluid from Untreated and Treated Patients with Nonspecific Vaginitis*, Kirk C.S. Chen, Patricia S. Forsyth, Thomas M. Buchanan, and King K. Holmes, J. Clin. Invest., vol. 63, May 1979, pp. 828-835.
Article—*Biochemical Diagnosis of Vaginitis: Determination of Diamines in Vaginal Fluid*, Kirk C.S. Chen, Richard Amsel, David A. Eschenbach, and King K. Holmes, The Journal of Infectious Diseases, vol. 145, No. 3, Mar. 1982, pp. 337-345.
Article—*Evaluation of a Time-Resolved Fluorescence Microscope Using a Phosphorescent Pt-Porphine Model System*, E. J. Hennink, R. de Haas, N. P. Verwoerd, and H. J. Tanke, Cytometry, vol. 24, 1996, pp. 312-320.
Article—*Fabrication of Surfaces Resistant to Protein Adsorption and Application to Two-Dimensional Protein Patterning*, Suresh K. Bhatia, John L. Teixeira, Mariquita Anderson, Lisa C. Shriver-Lake, Jeffrey M. Calvert, Jacque H. Georger, James J. Hickman, Charles S. Dulcey, Paul E. Schoen, and Frances S. Ligler, Analytical Biochemistry, vol. 208, 1993, pp. 197-205.
Article—*Immunoaffinity Based Phosphorescent Sensor Platform for the Detection of Bacterial Spores*, Peter F. Scholl, C. Brent Bargeron, Terry E. Phillips, Tommy Wong, Sala Abubaker, John D. Groopman, Paul T. Strickland, and Richard C. Benson, Proceedings of SPIE, vol. 3913, 2000, pp. 204-214.
Article—*Inert Phosphorescent Nanospheres as Markers for Optical Assays*, Jens M. Kümer, Ingo Klimant, Christian Krause, Harald Preu, Werner Kunz, and Ono S. Wolfbeis, Bioconjugate Chem., vol. 12, No. 6, 2001, pp. 883-889.
Article—*Longwave luminescent porphyrin probes*, Dmitry B. Papkovsky, Gelii P. Ponomarev, and Otto S. Wolfbeis, Spectrochimica Acta Part A 52, 1996, pp. 1629-1638.
Article—*Microfabrication by Microcontact Printing Of Self-Assembled Monolyaers*, James L. Wilbur, Armit Kumar, Enoch Kim, and George M. Whitesides, Advanced Materials, vol. 6, No. 7/8, 1994, pp. 600-604.
Article—*Modification of monoclonal and polyclonal IgG with palladium (II) coproporphyrin I: stimulatory and inhibitory functional effects induced by two different methods*, Sergey P. Martsev, Valery A. Preygèrzon, Yanina I. Mel'nikova, Zinaida I. Kravchuk, Gely V. Ponomarev, Vitaly E. Lunev, and Alexander P. Savitsky, Journal of Immunological Methods 186, 1996, pp. 293-304.
Article—*Monofunctional Derivatives of Coproporphyrins for Phosphorescent Labeling of Proteins and Binding Assays*, Tomás C. O'Riordan, Aleksi E. Soini, and Dmitri B. Papkovsky, Analytical Biochemistry, vol. 290, 2001, pp. 366-375.
Article—*Near Infrared Phosphorescent Metalloporphrins*, Alexander P. Savitsky Anna V. Savitskaja, Eugeny A. Lukjanetz, Svetlana N. Dashkevich, and Elena A. Makarova, SPIE, vol. 2980, pp. 352-357.
Article—*Performance Evaluation of the Phosphorescent Porphyrin Label: Solid-Phase Immunoassay of a-Fetoprotein*, Tomás C. O'Riordan, Aleksi E. Soini, Juhani T. Soini, and Dmitri B. Papkovsky, Analytical Chemistry, vol. 74, No. 22, Nov. 15, 2002, pp. 5845-5850.
Article—*Phosphorescent porphyrin probes in biosensors and sensitive bioassays*, D. B. Papkovsky, T. O'Riordan, and A. Soini, Biochemical Society Transactions, vol. 28, part 2, 2000, pp. 74-77.
Article—*Room-Temperature Phosphorescent Palladium—Porphine Probe for DNA Determination*, Montserrat Roza-Fernández, Maria Jesús Valencia-González, and Marta Elena Diaz-Garcia, Analytical Chemistry, vol. 69, No. 13, Jul. 1, 1997, pp. 2406-2410.
Article—*Self-Assembled Monolayer Films For Nanofabrication*, Elizabeth A. Dobisz, F. Keith Perkins, Susan L. Brandow, Jeffrey M. Calvert, and Christie R. K. Marrian, Mat. Res. Soc. Symp. Proc., vol. 380, 1995, pp. 23-34.
*AMI Screen Printers*—Product Information, 4 pages.
Wei, et al., U.S. Appl. No. 10/718,997, filed Nov. 21, 2003, Extension Of The Dynamic Detection Range Of Assay Devices.
Xuedong Song, U.S. Appl. No. 10/719,976, filed Nov. 21, 2003, Method For Extending The Dynamic Detection Range Of Assay Devices.

Yang, et al., U.S. Appl. No. 10/741,434, filed Dec. 19, 2003, Laminated Assay Devices.

Yang, et al., U.S. Appl. No. 10/742,589, filed Dec. 19, 2003, Flow Control Of Electrochemcial-Based Assay Devices.

Yang, et al., U.S. Appl. No. 10/742,590, filed Dec. 19, 2003, Flow-Through Assay Devices.

Xuedong Song, U.S. Appl. No. 10/718,989, filed Nov. 21, 2003, Membrane-Based Lateral Flow Assay Devices That Utilize Phosphorescent Detection.

Ning Wei, U.S. Appl. No. 10/718,996, filed Nov. 21, 2003, Method Of Reducing The Sensitivity Of Assay Devices.

David S. Cohen, U.S. Appl. No. 10/836,093, filed Apr. 30, 2004, Optical Detection Systems.

Boga, et al., U.S. Appl. No. 10/790,617, filed Mar. 1, 2004, Assay Devices Utilizing Chemichronic Dyes.

Abstract of DE10024145A1, Nov. 22, 2001.

Article—*Solid Substrate Phosphorescent Immunoassay Based On Bioconjugated Nanoparticles*, Baoquan Sun, Guangshun Yi, Shuying Zhao, Depu Chen, Yuxiang Zhou, and Jing Cheng, Analytical Letters, vol. 34, No. 10, 2001, pp. 1627-1637.

PCT Search Report and Written Opinion for PCT/US2004/013180, Aug. 17, 2004.

Article—*New Use of Cyanosilane Coupling Agent for Direct Binding of Antibodies to Silica Supports. Physicochemical Characterization of Molecularly Bioengineered Layers*, Sandrine Falipou, Jean-Marc Chovelon, Claude Martelet, Jacqueline Margonari and Dominique Cathignol, Bioconjugate Chem., vol. 10, No. 3, 1999, pp. 346-353.

PCT Search Report and Written Opinion for PCT/US2004/006412, Sep. 28, 2004.

PCT Search Report and Written Opinion for PCT/US2004/006414, Sep. 28, 2004.

* cited by examiner

POLYELECTROLYTIC INTERNAL CALIBRATION SYSTEM OF A FLOW-THROUGH ASSAY

RELATED APPLICATIONS

The present application is a continuation-in-part of U.S. application Ser. No. 10/035,014, filed on Dec. 24, 2001 now abandoned.

BACKGROUND OF THE INVENTION

Various analytical procedures and devices are commonly employed in flow-through assays to determine the presence and/or concentration of analytes that may be present in a test sample. For instance, immunoassays utilize mechanisms of the immune systems, wherein antibodies are produced in response to the presence of antigens that are pathogenic or foreign to the organisms. These antibodies and antigens, i.e., immunoreactants, are capable of binding with one another, thereby causing a highly specific reaction mechanism that can be used to determine the presence or concentration of that particular antigen in a biological sample.

There are several well-known immunoassay methods that use immunoreactants labeled with a detectable component so that the analyte can be detected analytically. For example, "sandwich-type" assays typically involve mixing the test sample with antibodies to the analyte. These antibodies are mobile and linked to a label or probe, such as dyed latex, a colloidal metal sol, or a radioisotope. This mixture is then contacted with a chromatographic medium containing a band or zone of immobilized antibodies to the analyte. The chromatographic medium is often in the form of a strip resembling a dipstick. When the complex of the analyte and the labeled antibody reaches the zone of the immobilized antibodies on the chromatographic medium, binding occurs and the bound labeled antibodies are localized at the zone. This indicates the presence of the analyte. This technique can be used to obtain quantitative or semi-quantitative results. Some examples of such sandwich-type assays are described in. by U.S. Pat. Nos. 4,168,146 to Grubb, et al. and 4,366,241 to Tom, et al.

An alternative technique is the "competitive-type" assay. In a "competitive-type" assay, the label is typically a labeled analyte or analyte-analogue that competes for binding of an antibody with any unlabeled analyte present in the sample. Competitive assays are typically used for detection of analytes such as haptens, each hapten being monovalent and capable of binding only one antibody molecule. Examples of competitive immunoassay devices are described in U.S. Pat. Nos. 4,235,601 to Deutsch, et al., 4,442,204 to Liotta, and 5,208,535 to Buechler, et al.

Many of these assays rely upon calibration to provide valid and meaningful results, particularly for semi-quantitative and quantitative detections. Specifically, either external or internal calibration systems are generally employed. In an external calibration system, a standard curve is usually obtained from standard samples containing a series of a known amount of analyte, and the results obtained from the samples are then compared with the standard curve to extract the presence and/or amount of the analyte in the sample. The external calibration method is relatively easy to design and simple to implement. However, it is often subject to interference from environmental and batch-to-batch variations, and is thus unreliable.

Conventional internal calibration systems, on the other hand, typically utilize a membrane that has a calibration zone and a detection zone on which the capturing reagent specific for the analyte is immobilized. Unfortunately, conventional internal calibration systems use biological capturing reagents (e.g., antibodies) in the calibration zone. Such biological capturing reagents are expensive, fragile, and difficult to control in terms of the amount of active species in the total mass. In addition, biological capturing agents also tend to degrade over time.

As such, a need currently exists for an accurate calibration system for flow-through assays that is readily controllable, inexpensive, and does not significantly degrade over time.

SUMMARY OF THE INVENTION

In accordance with one embodiment of the present invention, a flow-through assay (e.g., sandwich, competitive, etc.) is disclosed for detecting the presence or quantity of an analyte residing in a test sample. The assay comprises a porous membrane that is in fluid communication with a probe conjugate that contains a specific binding member and a detectable probe. For example, in some embodiments, the detectable probe is selected from the group consisting of chromogens, catalysts, fluorescent compounds, chemiluminescent compounds, radioactive labels, direct visual labels, liposomes, and combinations thereof. In one particular embodiment, the detectable probe comprises a latex microparticle.

The porous membrane also defines a detection zone that contains a capture reagent capable of binding to the analyte or probe conjugate. In some embodiments, for example, the capture reagent is selected from the group consisting of antigens, haptens, antibodies, and complexes thereof. The detection zone is capable of generating a detection signal to indicate the presence or absence of an analyte.

In addition, to assist in the determination of the amount of analyte present within the test sample, the porous membrane also defines a calibration zone in which a polyelectrolyte is substantially non-diffusively immobilized on the porous membrane. The calibration zone can contain one or multiple calibration regions (e.g., lines, dots, etc.) containing the polyelectrolyte. The polyelectrolyte is capable of binding to the probe conjugate. The polyelectrolyte used in the calibration zone can generally have any desired charge. Although not required, the charge of the polyelectrolyte can be selected to be opposite to the charge of the probes, thereby facilitating the formation of ionic bonds between the oppositely-charged molecules. For example, in some embodiments, the polyelectrolyte has a net positive charge. In such instances, the polyelectrolyte may, in some embodiments, be selected from the group consisting of polylysine, polyethylenimine, epichlorohydrin-functionalized polyamines and/or polyamidoamines, polydiallyidimethyl-ammonium chloride, cationic cellulose derivatives, and combinations thereof.

The immobilization of the polyelectrolyte within the calibration zone can generally be accomplished in a variety of different ways. For instance, in some embodiments, the charged polyelectrolyte molecule can form ionic bonds with certain functional groups present on the porous membrane. Likewise, to create a more permanent immobilization, the polyelectrolyte can sometimes form covalent bonds with functional groups present on the porous membrane. For example, in one embodiment, a crosslinkable polyelectrolyte, such as epichlorohydrin-functionalized polyamines and/or polyamidoamines, can be crosslinked onto the porous membrane.

Once the calibration zone generates a signal, it can then be compared to the detection signal to determine the relative amount of analyte present in the test sample. For example, in some embodiments, the calibration signals can be visually observed and compared to the detection signal. Moreover, the calibration signals can also be compared to the detection signal through the use of an instrument, such as a fluorescent reader, a color intensity reader, and the like. If desired, a calibration curve can be developed by plotting the intensity of the calibration signals versus known amounts of the analyte. Once generated, the curve can then be used to determine an unknown amount of the analyte within a test sample.

In accordance with another embodiment of the present invention, a flow-through assay for detecting the presence or quantity of an analyte residing in a test sample is disclosed. The flow-through assay comprises a porous membrane that is in fluid communication with probe conjugates that contain a specific binding member and a detectable probe. The probe conjugates are configured to combine with the analyte in the test sample when contacted therewith such that probe conjugate/analyte complexes and uncomplexed probe conjugates are formed. Further, the porous membrane defines a detection zone. A capture reagent is substantially non-diffusively immobilized on the porous membrane within the detection zone. The capture reagent is capable of binding to the probe conjugate/analyte complexes to generate a detection signal. A predetermined amount of polyelectrolyte is substantially non-diffusively immobilized on the porous membrane within the calibration zone. The calibration zone is capable of generating a calibration signal for comparison with the detection signal, wherein the relative amount of the analyte within the test sample is determined by comparing the detection signal to the calibration signal.

In accordance with another embodiment of the present invention, a flow-through assay for detecting the presence or quantity of an analyte (e.g., antigen) residing in a test sample is disclosed. The flow-through assay comprises a porous membrane that is fluid communication with probe conjugates containing a specific binding member and a detectable probe. For example, in one embodiment, the specific binding member is identical to the analyte. The porous membrane defines a detection zone in which a predetermined amount of capture reagent is substantially non-diffusively immobilized on the porous membrane. The capture reagent (e.g., antibody) is capable of binding to the analyte (e.g., antigen) such that the analyte of the test sample and probe conjugates compete for the predetermined amount of capture reagent. The detection zone is capable of generating a detection signal. A predetermined amount of polyelectrolyte is substantially non-diffusively immobilized on the porous membrane within the calibration zone. The calibration zone is capable of generating a calibration signal for comparison with the detection signal, wherein the relative amount of the analyte within the test sample is determined by comparing the detection signal to the calibration signal.

In accordance with still another embodiment of the present invention, a flow-through assay for detecting the presence or quantity of an analyte (e.g., antigen) residing in a test sample is disclosed. The assay comprises a porous membrane in communication with probe conjugates that contain a specific binding member (e.g., antibody) and a detectable probe. The probe conjugates are configured to combine with the analyte in the test sample when contacted therewith such that probe conjugate/analyte complexes and uncomplexed probe conjugates are formed. The porous membrane defines a detection zone in which a capture reagent is substantially non-diffusively immobilized on the porous membrane. The capture reagent (e.g., antigen) is capable of binding to the uncomplexed probe conjugates, wherein the detection zone is capable of generating a detection signal. A predetermined amount of polyelectrolyte is substantially non-diffusively immobilized on the porous membrane within the calibration zone. The calibration zone is capable of generating a calibration signal for comparison with the detection signal, wherein the relative amount of the analyte within the test sample is determined by comparing the detection signal to the calibration signal.

Other features and aspects of the present invention are discussed in greater detail below.

BRIEF DESCRIPTION OF THE DRAWINGS

A full and enabling disclosure of the present invention, including the best mode thereof, directed to one of ordinary skill in the art, is set forth more particularly in the remainder of the specification, which makes reference to the appended figures in which:

FIG. 4 is a top view of another embodiment of the present invention, in which

Figure 1:
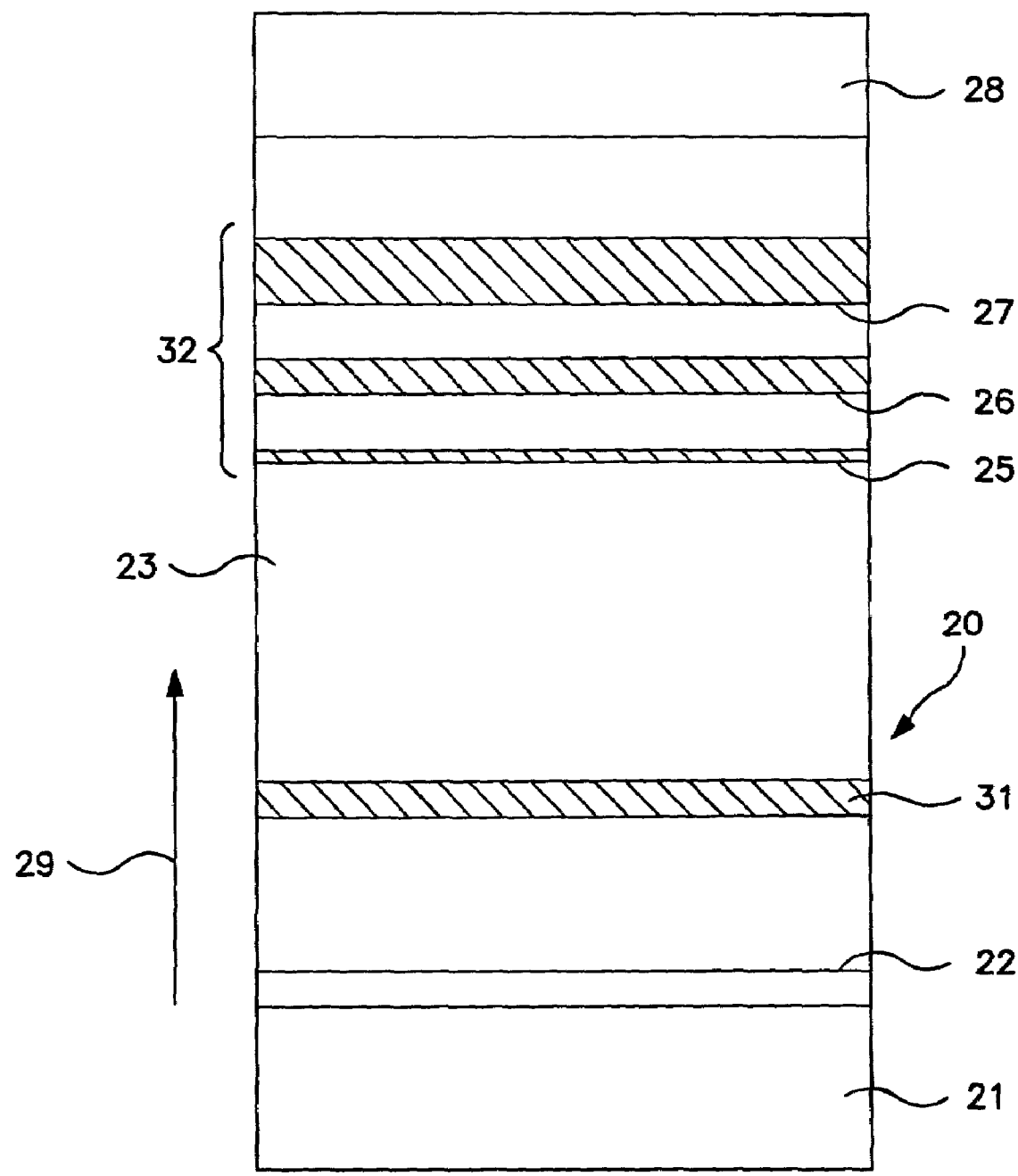
FIG. 1 is a top view of one embodiment of the present invention, showing a flow-through assay having three calibration lines in a calibration zone.

Repeat use of reference characters in the present specification and drawings is intended to represent same or analogous features or elements of the invention.

DETAILED DESCRIPTION OF REPRESENTATIVE EMBODIMENTS

Definitions

As used herein, the term "analyte" generally refers to a substance to be detected. For instance, analytes can includes antigenic substances, haptens, antibodies, and combinations thereof. Analytes include, but are not limited to, toxins, organic compounds, proteins, peptides, microorganisms, amino acids, nucleic acids, hormones, steroids, vitamins, drugs (including those administered for therapeutic purposes as well as those administered for illicit purposes), bacteria, virus particles and metabolites of or antibodies to any of the above substances. Specific examples of some analytes include ferritin; creatinine kinase MIB (CK-MB); digoxin; phenytoin; phenobarbitol; carbamazepine; vancomycin; gentamycin; theophylline; valproic acid; quinidine; leutinizing hormone (LH); follicle stimulating hormone (FSH); estradiol, progesterone; IgE antibodies; vitamin B2 micro-globulin; glycated hemoglobin (Gly. Hb); cortisol; digitoxin; N-acetylprocainamide (NAPA); procainamide; antibodies to rubella, such as rubella-IgG and rubella IgM; antibodies to toxoplasmosis, such as toxoplasmosis IgG (Toxo-IgG) and toxoplasmosis IgM (Toxo-IgM); testosterone; salicylates; acetaminophen; hepatitis B virus surface antigen (HBsAg); antibodies to hepatitis B core antigen, such as anti-hepatitis B core antigen IgG and IgM (Anti-HBC); human immune deficiency virus 1 and 2 (HIV 1 and 2); human T-cell leukemia virus 1 and 2 (HTLV); hepatitis B e antigen (HBeAg); antibodies to hepatitis B e antigen (Anti-HBe); thyroid stimulating hormone (TSH); thyroxine (T4); total triiodothyronine (Total T3); free triiodothyronine (Free T3); carcinoembryoic antigen (CEA); and alpha fetal protein (AFP). Drugs of abuse and controlled substances include, but are not intended to be limited to, amphetamine; methamphetamine; barbiturates, such as amobarbital, secobarbital, pentobarbital, phenobarbital, and barbital; benzodiazepines, such as librium and valium; cannabinoids, such as hashish and marijuana; cocaine; fentanyl; LSD; methaqualone; opiates, such as heroin, morphine, codeine, hydromorphone, hydrocodone, methadone, oxycodone, oxymorphone and opium; phencyclidine; and propoxyhene. Other potential analytes may be described in U.S. Pat. No. 4,366,241 to Tom et al.

As used herein, the term "test sample" generally refers to a material suspected of containing the analyte. The test sample can be used directly as obtained from the source or following a pretreatment to modify the character of the sample. The test sample can be derived from any biological source, such as a physiological fluid, including, blood, saliva, ocular lens fluid, cerebral spinal fluid, sweat, urine, milk, ascites fluid, raucous, synovial fluid, peritoneal fluid, amniotic fluid or the like. The test sample can be pretreated prior to use, such as preparing plasma from blood, diluting viscous fluids, and the like. Methods of treatment can involve filtration, distillation, concentration, inactivation of interfering components, and the addition of reagents. Besides physiological fluids, other liquid samples can be used such as water, food products and the like for the performance of environmental or food production assays. In addition, a solid material suspected of containing the analyte can be used as the test sample. In some instances it may be beneficial to modify a solid test sample to form a liquid medium or to release the analyte.

DETAILED DESCRIPTION

Reference now will be made in detail to various embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents.

In general, the present invention is directed to an internal calibration system for flow-through assays. In particular, the present invention employs the use of one or more polyelectrolytes within a calibration zone defined by a porous membrane of the assay. The polyelectrolytes are configured to bind to probes and/or probe conjugates flowing through the assay, thereby generating a calibration signal for comparison with a corresponding detection signal. It has been discovered that, not only does the internal calibration system provide an accurate method of determining the presence of an analyte in a test sample, but the materials used in the system are also readily controllable, inexpensive, and do not tend to degrade over time.

Figure 2:
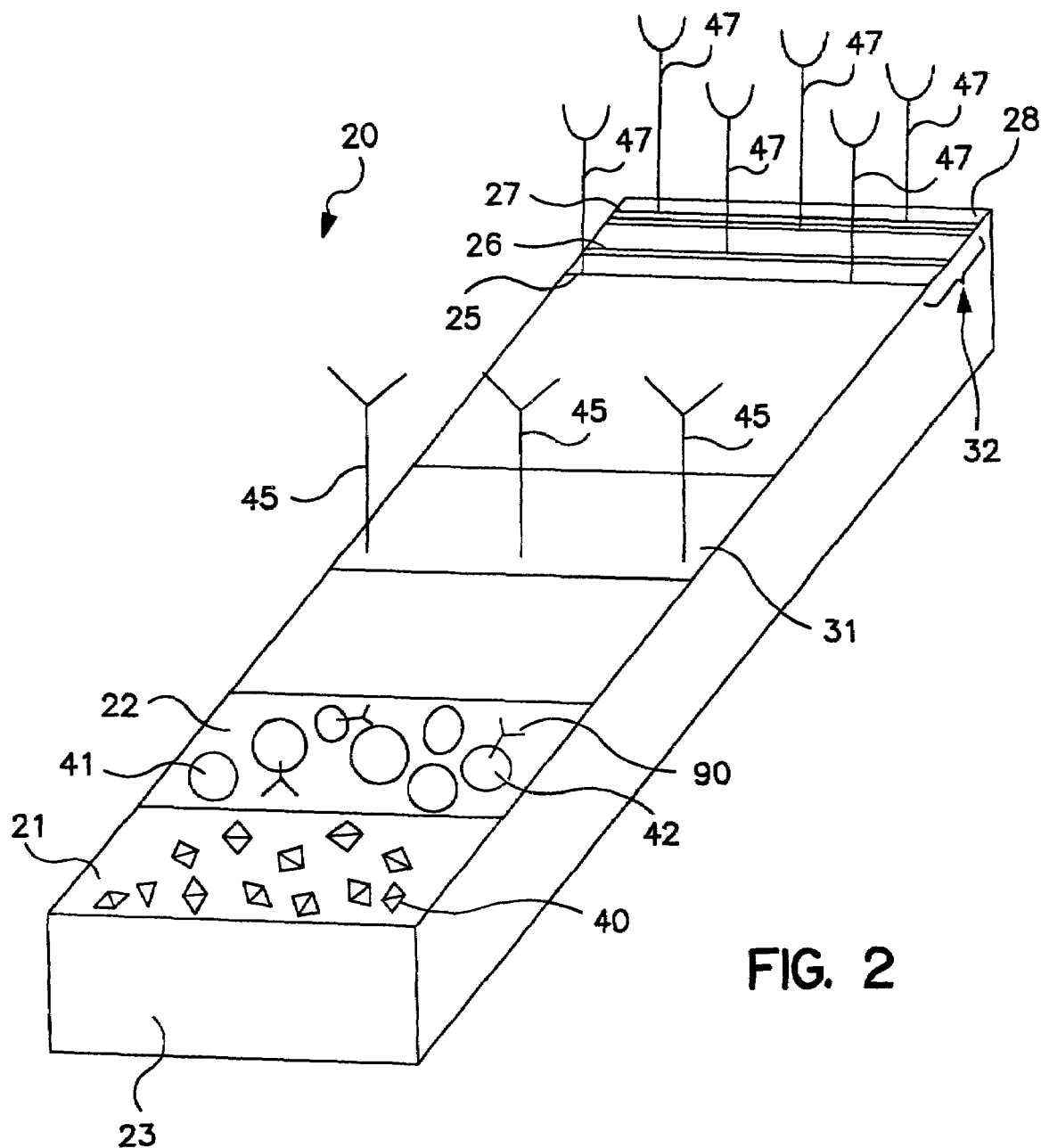
FIG. 2 is a perspective schematic view of one embodiment of a flow-through assay of the present invention, showing the membrane strip after a test sample containing analyte has been applied to the sampling pad.
Figure 3:
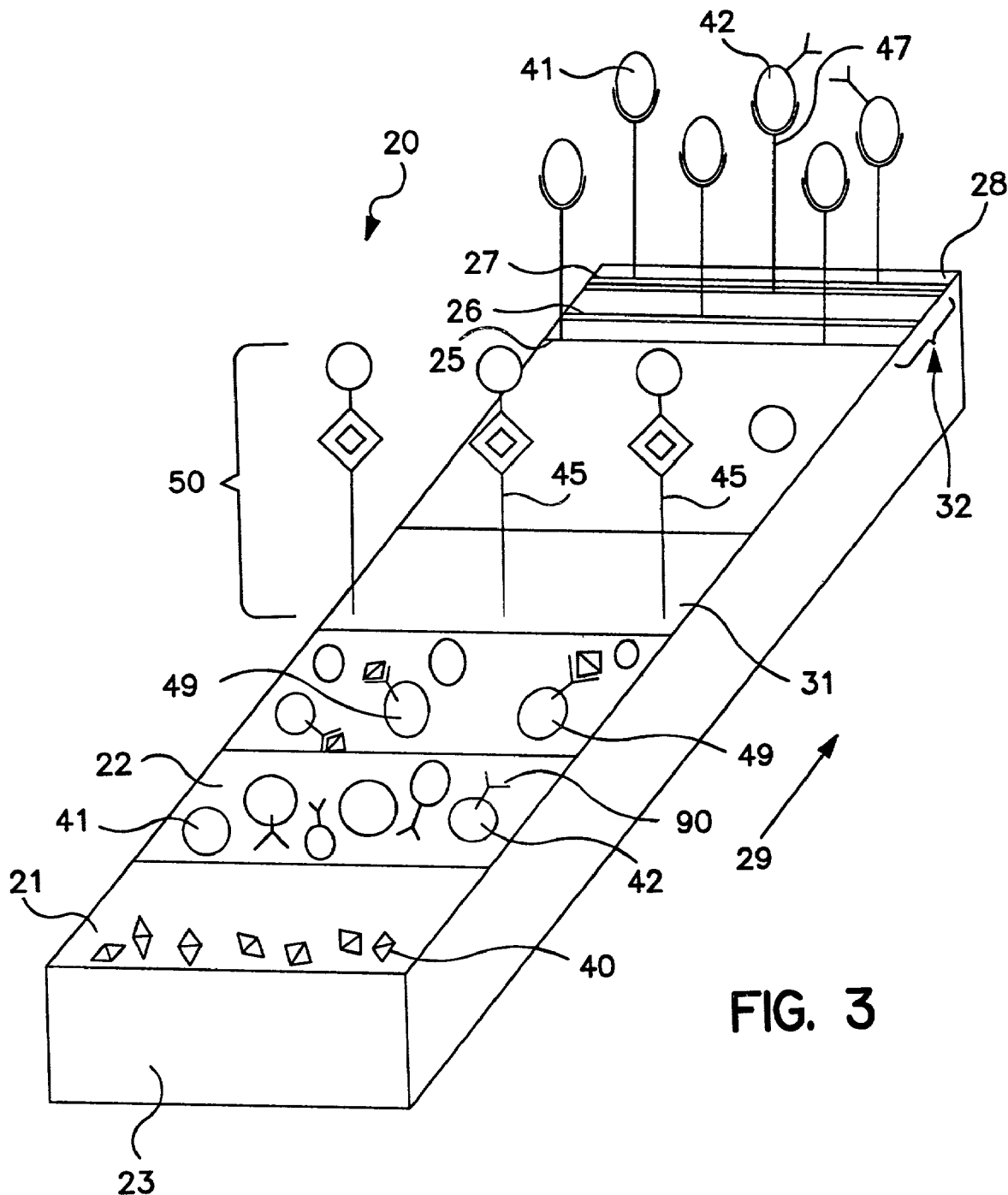
FIG. 3 illustrates the lateral assay shown in FIG. 2, but with the test sample migrated through the assay.

Referring to FIGS. 1-3, for instance, one embodiment of a sandwich-type flow-through assay 20 that can be formed according to the present invention will now be described in more detail. As shown, the assay 20 is contains a porous membrane 23 optionally supported by a rigid material (not shown). In general, the porous membrane 23 can be made from any of a variety of materials through which the test sample is capable of passing. For example, the materials used to form the porous membrane 23 can include, but are not limited to, natural, synthetic, or naturally occurring materials that are synthetically modified, such as polysaccharides (e.g., cellulose materials such as paper and cellulose derivatives, such as cellulose acetate and nitrocellulose); silica; inorganic materials, such as deactivated alumina, diatomaceous earth, $MgSO_4$, or other inorganic finely divided material uniformly dispersed in a porous polymer matrix, with polymers such as vinyl chloride, vinyl chloride-propylene copolymer, and vinyl chloride-vinyl acetate copolymer; cloth, both naturally occurring (e.g., cotton) and synthetic (e.g., nylon or rayon); porous gels, such as silica gel, agarose, dextran, and gelatin; polymeric films, such as polyacrylamide; and the like. In one particular embodiment, the porous membrane 23 is formed from nitrocellulose and/or polyester sulfone materials. It should be understood that the term "nitrocellulose" refers to nitric acid esters of cellulose, which may be nitrocellulose alone, or a mixed ester of nitric acid and other acids, such as aliphatic carboxylic acids having from 1 to 7 carbon atoms.

To initiate the detection of an analyte 40 within the test sample, a user may directly apply the test sample to a portion of the porous membrane 23 through which it can then travel to reach one or more detection and calibration zones (described below). Alternatively, the test sample may first be applied to a sampling pad that is in fluid communication with the porous membrane 23. For example, as shown in FIGS. 1-3, the lateral flow assay 20 can contain a sampling pad 21 generally configured to receive the test sample. Some suitable materials that can be used to form the sampling pad 21 include, but are not limited to, nitrocellulose, cellulose, porous polyethylene pads, and glass fiber filter paper. If desired, the sampling pad 21 may also contain one or more assay pretreatment reagents, either diffusively or non-diffusively attached thereto.

In the illustrated embodiment, the test sample travels from the sampling pad 21 to a conjugate pad 22 (as shown by the directional arrow 29 in FIG. 1) that is placed in communication with one end of the sampling pad 21. The conjugate pad 22 is formed from a material through which the test sample is capable of passing. For example, in one embodiment, the conjugate pad 22 is formed from glass fibers.

Besides simply allowing the test sample to pass therethrough, the conjugate pad 22 also typically performs other functions as well. For example, in some embodiments, various probes 41 (see FIG. 2) are releasibly applied to the conjugate pad 22. While contained on the conjugate pad 22, these probes 41 remain available for binding with the analyte 40 as the analyte 40 passes from the sample pad 21 through the conjugate pad 22. Upon binding with the analyte 40, the probes 41 can later serve to identify (e.g., visually, etc.) the presence of the analyte 40 in the detection zone of the assay 20.

Any substance generally capable of producing a signal that is visually detectable or detectable by an instrumental device may be used as the probes 41. Various suitable probes can include chromogens; catalysts; fluorescent compounds; chemiluminescent compounds; radioactive labels; direct visual labels, including colloidal metallic and non-metallic particles (e.g., gold), dye particles, enzymes or substrates, or organic polymer latex particles; liposomes or other vesicles containing signal producing substances; and the like. For instance, some enzymes suitable for use as probes are disclosed in U.S. Pat. No. 4,275,149 to Litman, et al., which is incorporated herein in its entirety by reference thereto for all purposes. One example of an enzyme/substrate probe system is the enzyme alkaline phosphatase and the substrate nitro blue tetrazolium-5-bromo-4-chloro-3-indolyl phosphate, or derivative or analog thereof, or the substrate 4-methylumbelliferyl-phosphate. In an alternative probe system, the probe can be a fluorescent compound where no enzymatic manipulation is required to produce a detectable signal. Fluorescent molecules, such as fluorescein, phycobiliprotein, rhodamine and their derivatives and analogs, are suitable for use as probes in this reaction. Commercially available examples of such fluorescent materials include fluorescent carboxylated microspheres sold by Molecular Probes, Inc. under the trade names "FluoSphere" (Red 580/605) and "TransfluoSphere" (543/620), as well as "Texas Red" and 5- and 6-carboxytetramethylrhodamine, which are also sold by Molecular Probes, Inc.

A visually detectable, colored microparticle (sometimes referred to as "beads" or "microbeads") can also be used as a probe, thereby providing for a direct colored readout of the presence or concentration of the analyte in the sample without the need for further signal producing reagents. In some instances, the particles that are used in a quantitative assay can also contribute a signal (e.g., light absorption) that would cause the zone in which the particles are located to have a different signal than the rest of the membrane 23.

The type of microparticles utilized for the probes 41 may also vary. For instance, naturally occurring microparticles, such as nuclei, mycoplasma, plasmids, plastids, mammalian cells (e.g., erythrocyte ghosts), unicellular microorganisms (e.g., bacteria), polysaccharides (e.g., agarose), and the like, can be used. Further, synthetic microparticles may also be utilized. For example, in one embodiment, synthetic latex microparticles that are colored with a dye are utilized as the probes 41. Although any latex microparticle capable of adsorbing or covalently bonding to a binding partner may be used in the present invention, the latex microparticles are typically formed from polystyrene, butadiene styrenes, styreneacrylic-vinyl terpolymer, polymethylmethacrylate, polyethylmethacrylate, styrene-maleic anhydride copolymer, polyvinyl acetate, polyvinylpyridine, polydivinylbenzene, polybutyleneterephthalate, acrylonitrile, vinylchloride-acrylates, and the like, or an aldehyde, carboxyl, amino, hydroxyl, or hydrazide derivative thereof. Other suitable microparticles may be described in U.S. Pat. Nos. 5,670,381 to Jou, et al. and 5,252,459 to Tarcha, et al., which are incorporated herein in their entirety by reference thereto for all purposes. Commercially available examples of suitable colored, latex microparticles include carboxylated latex beads sold by Bang's Laboratory, Inc.

When utilized, the mean diameter of particulate probes 41 may generally vary as desired depending on factors such as the type of particle chosen, the pore size of the membrane, and the membrane composition. For example, in some embodiments, the mean diameter of the particulate probes 41 ranges from about 0.01 microns to about 100 microns, and in some embodiments, from about 0.1 microns to about 75 microns. In one particular embodiment, the particulate probes 41 have a mean diameter of about 0.3 microns. In such instances, the membrane 23 can have a pore size of from about 0.1 to about 0.3 microns.

When deposited on the conjugate pad 22, the probes 41 may be capable of directly bonding (covalently or non-covalently) with the analyte 40. However, it is often desired to modify the probes 41 in some manner so that they are more readily able to bond to the analyte 40. In such instances, the probes 41 can be modified with certain specific binding members 90 that are non-covalently (e.g., adsorbed) and/or covalently attached thereto to form probe conjugates 42.

Specific binding members generally refer to a member of a specific binding pair, i.e., two different molecules where one of the molecules chemically and/or physically binds to the second molecule. For instance, immunoreactive specific binding members can include antigens, haptens, antibodies, and complexes thereof, including those formed by recombinant DNA methods or peptide synthesis. An antibody can be a monoclonal or polyclonal antibody, a recombinant protein or a mixture(s) or fragment(s) thereof, as well as a mixture of an antibody and other specific binding members. The details of the preparation of such antibodies and their suitability for use as specific binding members are well known to those skilled in the art.

Other common specific binding pairs include but are not limited to, biotin and avidin, carbohydrates and lectins, complementary nucleotide sequences (including probe and capture nucleic acid sequences used in DNA hybridization assays to detect a target nucleic acid sequence), complementary peptide sequences including those formed by recombinant methods, effector and receptor molecules, hormone and hormone binding protein, enzyme cofactors and enzymes, enzyme inhibitors and enzymes, and the like. Furthermore, specific binding pairs can include members that are analogs of the original specific binding member. For example, a derivative or fragment of the analyte, i.e., an analyte-analog, can be used so long as it has at least one epitope in common with the analyte.

The specific binding members 90 can generally be attached to the probes 41 using any of a variety of well-known techniques. For instance, when using latex microparticles as the probes 41, covalent attachment of the specific binding members 90 thereto can be accomplished using carboxylic, amino, aldehyde, bromoacetyl, iodoacetyl, thiol, epoxy and other reactive or linking functional groups, as well as residual free radicals and radical cations, through which a protein coupling reaction can be accomplished. A surface functional group can also be incorporated as a functionalized co-monomer because the surface of the latex microparticle can contain a relatively high surface concentration of polar groups. In addition, although latex microparticle probes are typically functionalized after synthesis, in certain cases, such as poly(thiophenol), the microparticles are capable of direct covalent linking with a protein without the need for further modification.

Thus, referring again to FIGS. 2 and 3, a test sample containing an analyte 40 can initially be applied to the sampling pad 21. From the sampling pad, the test sample can then travel to the conjugate pad 22, where the analyte 40 binds to the specific binding member 90 of a probe conjugate 42 to form a probe conjugate/analyte complex 49. Moreover, because the conjugate pad 22 is in fluid communication with the porous membrane 23, the probe conjugate/analyte complex 49 can migrate from the conjugate pad 22 to a detection zone 31 present on the porous membrane 23.

The detection zone 31 may contain an immobilized capture reagent 45. Although not required, it may be desired that the capture reagents 45 be formed from the same class or category of materials (e.g., antibodies) as the specific binding members 90 used to form the probe conjugates 42. These capture reagents 45 serve as stationary binding sites for the probe conjugate/analyte complexes 49. In some instances, the analytes 40, such as antibodies, antigens, etc., have two binding sites. Upon reaching the detection zone 31, one of these binding sites is occupied by the specific binding member 90 of the probe conjugate/analyte complex 49. However, the free binding site of the analyte 40 can bind to the immobilized capture reagent 45. Upon being bound to the immobilized capture reagent 45, the probe conjugate 42 of a newly formed ternary complex 50 signals the presence of the analyte 40, either visually or through other methods of detection (e.g., instruments, etc.). Thus, to determine whether a particular analyte 40 is present within a test sample, a user can simply analyze the detection zone 31.

However, although a detection zone may indicate the presence of an analyte, it is often difficult to determine the relative concentration of the analyte within a test sample using solely a detection zone. Thus, in accordance with the present invention, the assay also includes a calibration zone that may be compared to the detection zone for determining the concentration of a particular analyte within a test sample. For instance, referring again to FIGS. 1-3, one embodiment of a flow-through assay 20 that includes a calibration zone 32 is illustrated. In this embodiment, the calibration zone 32 is formed on the porous membrane and is positioned downstream from the detection zone 31. The calibration zone 32 is provided with a binder 47 that is capable of binding to any remaining probes 41 and/or probe conjugates 42 that pass through the length of the membrane 23. In particular, upon being contacted with the test sample, any probes 41 and/or probe conjugates 42 that do not bind to the analyte 40 migrate through the detection zone 31 with the complexes 49. In the detection zone 31, as set forth above, the complexes 49 bind to capture reagents 45 and remain immobilized. However, the unbound probes 41 and/or probe conjugates 42 continue to migrate through the detection zone 31 and enter the calibration zone 32 of the porous membrane 23. At the calibration zone 32, these unbound probes 41 and/or probe conjugates 42 then bind to the binders 47. When immobilized in the calibration zone 32, the probes 41 and/or probe conjugates 42 are observable, either visually or by other methods, so that a user can compare the signal intensity in the detection zone 31 to the signal intensity in the calibration zone 32.

In accordance with one embodiment of the present invention, the binders 47 include a polyelectrolyte that can bind to the probes 41 and/or probe conjugates 42. The polyelectrolytes can have a net positive or negative charge, as well as a net charge that is generally neutral. For instance, some suitable examples of polyelectrolytes having a net positive charge include, but are not limited to, polylysine (commercially available from Sigma-Aldrich Chemical Co., Inc. of St. Louis, Mo.), polyethylenimine; epichlorohydrin-functionalized polyamines and/or polyamidoamines, such as poly(dimethylamine-co-epichlorohydrin); polydiallyidimethyl-ammonium chloride; cationic cellulose derivatives, such as cellulose copolymers or cellulose derivatives grafted with a quaternary ammonium water-soluble monomer; and the like. In one particular embodiment, CelQuat® SC-230M or H-100 (available from National Starch & Chemical, Inc.), which are cellulosic derivatives containing a quaternary ammonium water-soluble monomer, can be utilized. Moreover, some suitable examples of polyelectrolytes having a net negative charge include, but are not limited to, polyacrylic acids, such as poly(ethylene-co-methacrylic acid, sodium salt), and the like. It should also be understood that other polyelectrolytes may also be utilized in the present invention, such as amphiphilic polyelectrolytes (i.e., having polar an non-polar portions). For instance, some examples of suitable amphiphilic polyelectrolytes include, but are not limited to, poly(styryl-b-N-methyl 2-vinyl pyridinium iodide) and poly (styryl-b-acrylic acid), both of which are available from Polymer Source, Inc. of Dorval, Canada.

Although any polyelectrolyte may generally be used, the polyelectrolyte selected for a particular application may vary depending on the nature of the probes/probe conjugates, the porous membrane, and the like. In particular, the distributed charge of a polyelectrolyte allows it to bind to substances having an opposite charge. Thus, for example, polyelectrolytes having a net positive charge are often better equipped to bind with probes 41 and/or probe conjugates 42 that are negatively charged, while polyelectrolytes that have a net negative charge are often better equipped to bind to probes 41 and/or probe conjugates 42 that are positively charged. Thus, in such instances, the ionic interaction between these molecules allows the required binding to occur within the calibration zone 32. Nevertheless, although ionic interaction is primarily utilized to achieve the desired binding in the calibration zone 32, it has also been discovered that polyelectrolytes can also bind with probes 41 and/or probe conjugates 42 having a similar charge.

Because the polyelectrolyte is designed to bind to the probes 41 and/or probe conjugates 42 to provide a calibration signal, it is typically desired that the polyelectrolyte be substantially non-diffusively immobilized on the surface of the porous membrane 23. Otherwise, the probes 41 and/or probe conjugates 42 would not be readily detectable by a user seeking to calibrate the assay. Thus, the polyelectrolytes can be applied to the porous membrane 23 in such a manner that the polyelectrolytes do not substantially diffuse into the matrix of the porous membrane 23. In particular, the polyelectrolytes typically form an ionic and/or covalent bond with functional groups present on the surface of the porous membrane 23 so that they remain immobilized thereon. Although not required, the formation of covalent bonds between the polyelectrolyte and the porous membrane 23 may be desired to more permanently immobilize the polyelectrolyte thereon.

For example, in one embodiment, the monomers used to form the polyelectrolyte are first formed into a solution and then applied directly to the porous membrane 23. Various solvents (e.g., organic solvents, water, etc.) may be utilized to form the solution. Once applied, the polymerization of the monomers is initiated using heat, electron beam radiation, free radical polymerization, and the like. In some instances, as the monomers polymerize, they form covalent bonds with certain functional groups of the porous membrane 23, thereby immobilizing the resulting polyelectrolyte thereon. For example, in one embodiment, an ethyleneimine monomer can form a covalent bond with a carboxyl group present on the surface of some porous membranes (e.g., nitrocellulose).

In another embodiment, the polyelectrolyte can be formed prior to application to the porous membrane 23. If desired, the polyelectrolyte may first be formed into a solution using organic solvents, water, and the like. Thereafter, the polyelectrolytic solution is applied directly to the porous membrane 23 and then dried. Upon drying, the polyelectrolyte may, as described above, form an ionic bond with certain functional groups present on the surface of the porous membrane 23 that have a charge opposite to the polyelectrolyte. For example, in one embodiment, positively-charged polyethyleneimine can form an ionic bond with negatively-charged carboxyl groups present on the surface of some porous membranes (e.g., nitrocellulose).

In addition, the polyelectrolyte may also be crosslinked to the porous membrane 23 using various well-known techniques. For example, in some embodiments, epichlorohydrin-functionalized polyamines and/or polyamidoamines can be used as a crosslinkable, positively-charged polyelectrolyte.

Examples of these materials are described in U.S. Pat. Nos. 3,700,623 to Keim and 3,772,076 to Keim, 4,537,657 to Keim, which are incorporated herein in their entirety by reference thereto for all purposes and are believed to be sold by Hercules, Inc., Wilmington, Del. under the Kymene™ trade designation. For instance, Kymene™ 450 and 2064 are epichlorohydrin-functionalized polyamine and/or polyamidoamine compounds that contain epoxide rings and quaternary ammonium groups that can form covalent bonds with carboxyl groups present on certain types of porous membranes (e.g., nitrocellulose) and crosslink with the polymer backbone of the porous membrane when cured. In some embodiments, the crosslinking temperature can range from about 50° C. to about 120° C. and the crosslinking time can range from about 10 to about 600 seconds.

Although various techniques for non-diffusively immobilizing polyelectrolytes on the porous membrane 23 have been described above, it should be understood that any other technique for non-diffusively immobilizing polyelectrolytic compounds can be used in the present invention. In fact, the aforementioned methods are only intended to be exemplary of the techniques that can be used in the present invention. For example, in some embodiments, certain components may be added to the polyelectrolyte solution that can substantially inhibit the diffusion of such polyelectrolytes into the matrix of the porous membrane 23.

The calibration zone 32 may generally provide any number of distinct calibration regions so that a user can better determine the concentration of a particular analyte within a test sample. In most embodiments, for example, the calibration zone 32 includes two or more calibration distinct calibration regions (e.g., lines, dots, etc.). For instance, in the illustrated embodiment, at least three calibration regions 25, 26, and 27 in the form of lines are utilized. As shown in FIGS. 1-3, the calibration regions 25, 26, and/or 27 may be disposed in the form of lines in a direction that is substantially perpendicular to the flow of the test sample through the assay 20.

Figure 4A:
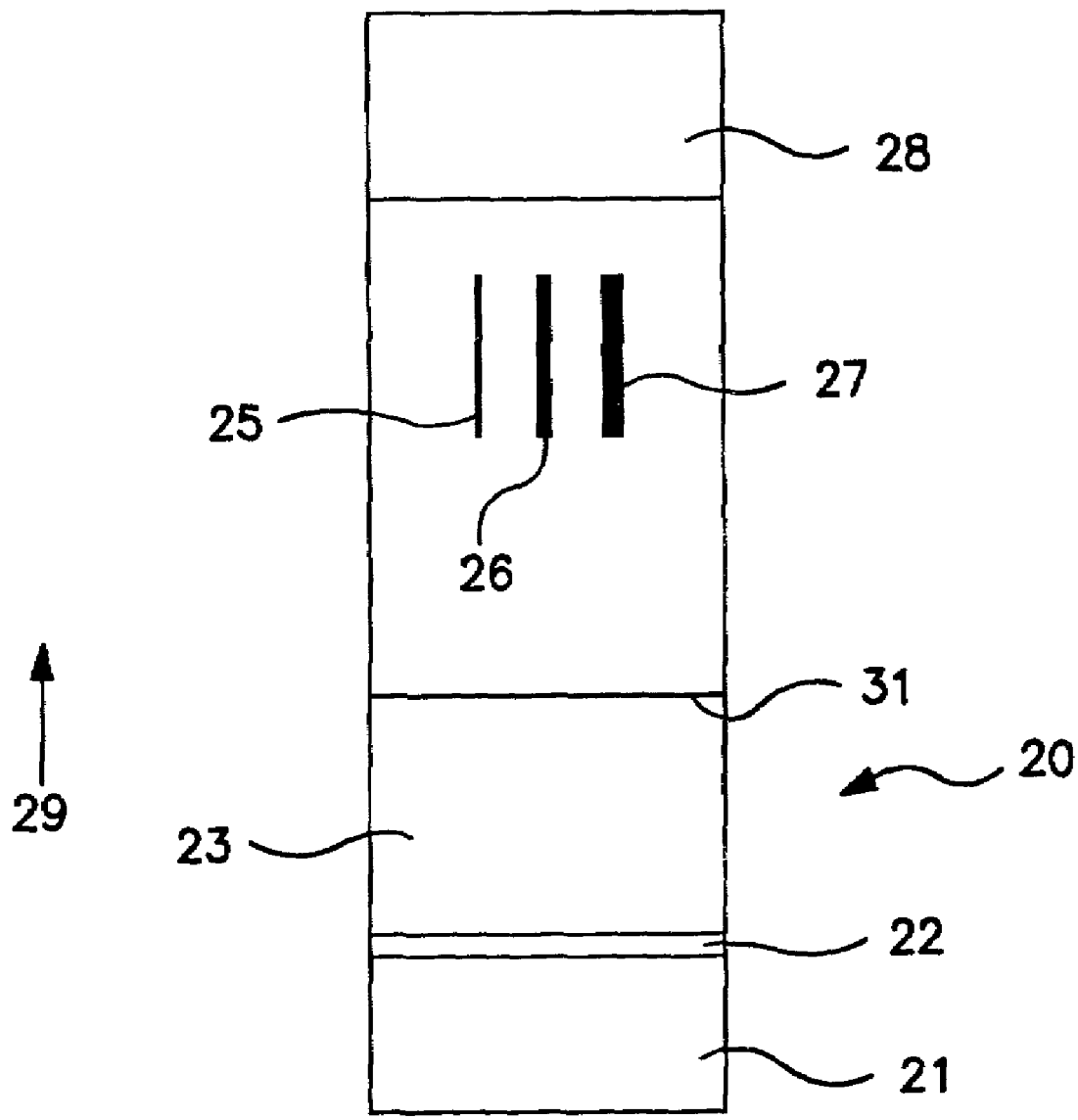
FIG. 4A shows calibration lines substantially parallel to the flow of the analyte and FIG. 4B shows calibration dots substantially parallel to the flow of the analyte.
Figure 4B:
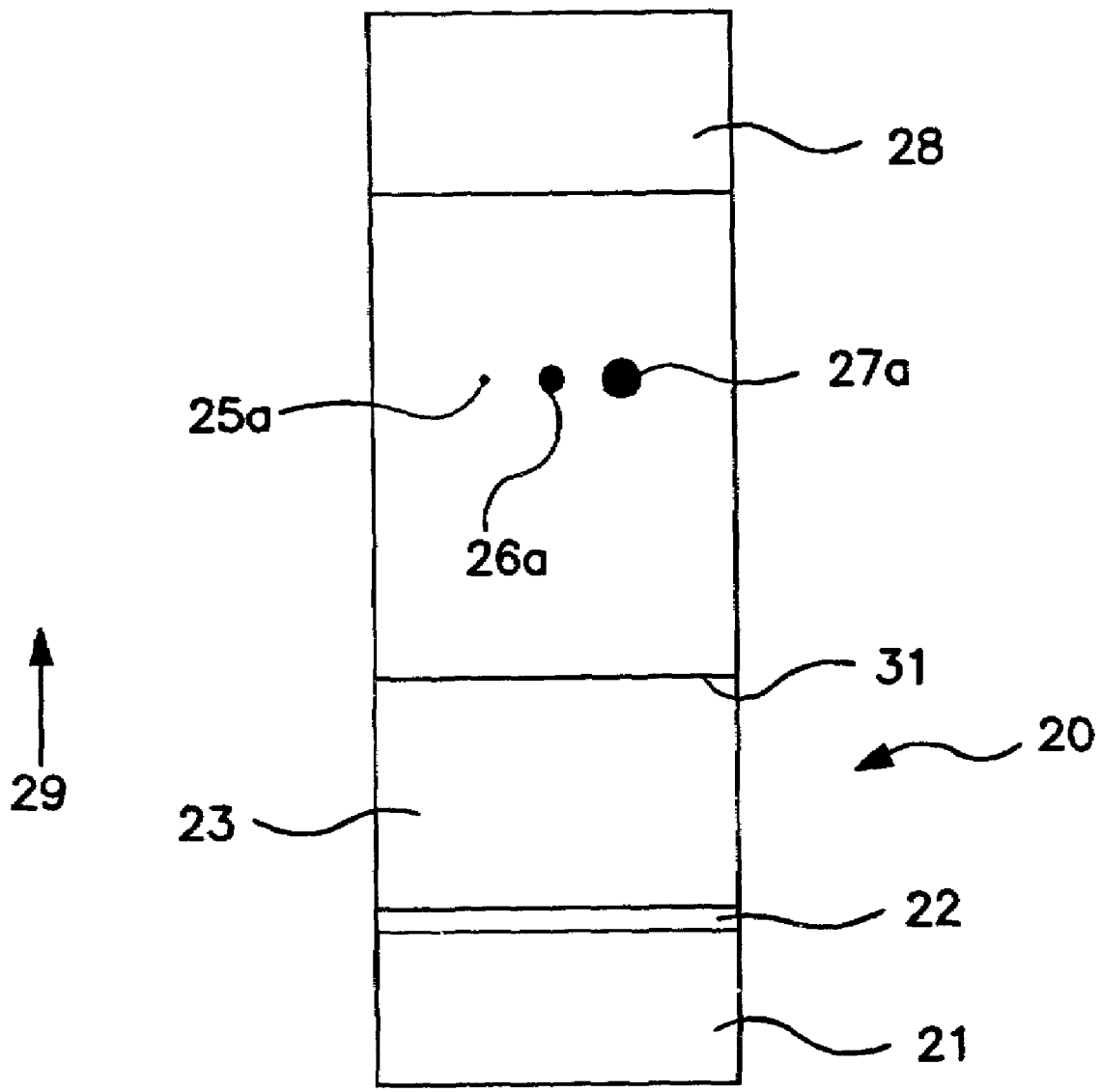

Likewise, in some embodiments, such as shown in FIG. 4A, the calibration regions 25, 26, and/or 27 can be disposed in the form of lines in a direction that is substantially parallel to the flow of the test sample through the assay. In yet another embodiment, such as shown in FIG. 4B, three calibration regions 25a, 26a, and 27a are disposed in the form of dots in a direction that is substantially parallel to the flow of the test sample through the assay. In such instances, a user may be able to compare the calibration signal to the detection signal in a lesser amount of time because each of the calibration regions simultaneously generate a calibration signal.

The calibration regions 25, 26, and 27 may be pre-loaded on the porous membrane 23 with different amounts of the polyelectrolyte so that a different signal intensity is generated by each calibration region 25, 26, and 27 upon migration of the probes 41 and/or probe conjugates 42. The overall amount of the polyelectrolyte within each calibration region can be varied by utilizing calibration regions of different sizes and/or by varying the solution concentration or volume of the polyelectrolyte in each calibration region. Generally speaking, the concentration of a polyelectrolyte within a given calibration region can range from about 0.01% to about 25% by weight of the solution.

If desired, an excess of probe molecules can be employed in the assay 20 so that each calibration region 25, 26, and 27 reaches its full and predetermined potential for signal intensity. That is, the amount of probes 41 that are deposited upon calibration regions 25, 26, and 27 are predetermined because the amount of the polyelectrolyte employed on the calibration regions 25, 26, and 27 is set at a predetermined and known level. A comparison may be made between the intensity levels of the calibration regions 25, 26, and 27 and the detection line 24 to calculate the amount of analyte 40 present in the test sample. This comparison step may occur visually, with the aid of a reading device, or using other techniques.

Figure 5:
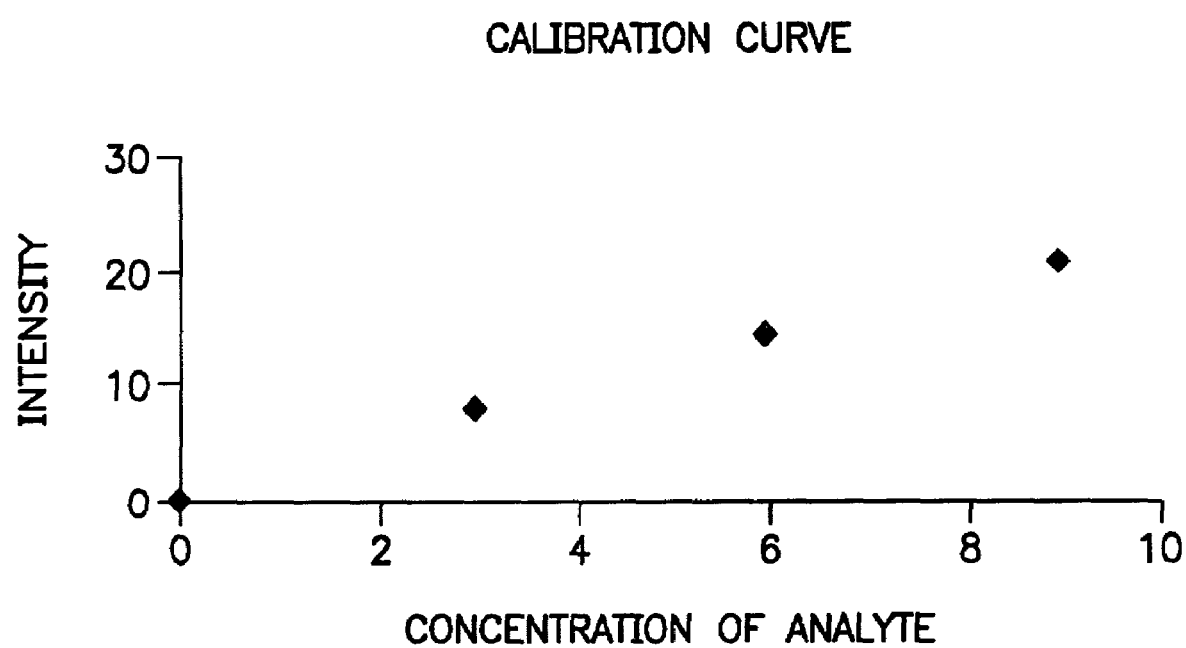
FIG. 5 shows a calibration curve that may be used in one embodiment of the present invention.

Calibration and sample testing may be conducted under approximately the same conditions at the same time, thus providing reliable quantitative results, with increased sensitivity. The assay 20 may also be employed for semi-quantitative detection. Specifically, when multiple calibration regions 25, 26, and 27 provide a range of signal intensities, the signal intensity of the detection zone 31 can be compared (e.g., visually) with the intensity of the calibration regions 25, 26, and 27. Based upon the intensity range in which the detection zone 31 falls, the general concentration range for the analyte 40 may be determined. If desired, the signal ratio between the detection zone 31 and the calibration regions 25, 26, and 27 may be plotted versus analyte concentration for a range of known analyte concentrations to generate a calibration curve, such as shown in FIG. 5. To determine the quantity of an unknown test sample, the signal ratio may then be converted to analyte concentration according to the calibration curve. Moreover, when using fluorescence to determine the amount of analyte 40 in a test sample, a receiver or a receiving device can be used to measure the amount of fluorescence generated in the detection zone 31 and the calibration zone 32, and thereafter make the appropriate comparison to determine the quantity of analyte in a given test sample.

Beside the above-mentioned components, the flow-through assay 20 may also contain additional components. For example, referring again to FIGS. 1-3, the assay 20 can also contain a wicking pad 28. The wicking pad 28 generally receives fluid that has migrated through the entire porous membrane 23. As is well known in the art, the wicking pad 28 can assist in promoting capillary action and fluid flow through the membrane 23.

Although various embodiments of assay configurations have been described above, it should be understood, that an assay of the present invention may generally have any configuration desired, and need not contain all of the components described above. Further, other well-known components of assays not specifically referred to herein may also be utilized in the present invention. For example, various assay configurations are described in U.S. Pat. Nos. 5,395,754 to Lambotte, et al.; 5,670,381 to Jou, et al.; and 6,194,220 to Malick, et al., which are incorporated herein in their entirety by reference thereto for all purposes. In addition, it should also be understood that competitive assays may also be formed according to the present invention. Techniques and configurations of competitive assays are well known to those skilled in the art.

For instance, in one embodiment, the flow-through assay 20 described above and illustrated in FIGS. 1-3 can be easily modified to form a competitive assay by utilizing probe conjugates 42 that contain specific binding members 90 identical to the analyte 40. As a result, the analyte 40 and probe conjugates 42 will compete for a predetermined number of capture reagents 45 in the detection zone 31. Generally speaking, because the analyte 40 is unbound, it will move faster through the porous membrane and occupy a greater number of binding sites in the detection zone 31. Any unbound probe conjugates 42 will then travel to the calibration zone 32 where they can bind with the polyelectrolyte. The signal thus generated in the calibration zone 32 can be compared to the signal generated in the detection zone 31, wherein the relative amount of analyte in the test sample is inversely proportional to the intensity of the detection signal and directly proportional to the intensity of the calibration signal.

Likewise, in another embodiment, a competitive assay can be formed by utilizing capture reagents 45 that are identical to the analyte 40. Thus, in this embodiment, the probe conjugates 42 initially bind to the analyte 40 to form ternary complexes 49. The unbound probe conjugates 42 and ternary complexes 49 then migrate to the detection zone 31, where the unbound probe conjugates 42 bind to the capture reagent. Any remaining unbound probe conjugates 42 and the ternary complexes 49 will then migrate to the calibration zone 32, where they compete for a predetermined amount of the polyelectrolyte. The signal thus generated in the calibration zone 32 can be compared to the signal generated in the detection zone 31, wherein the relative amount of analyte in the test sample is inversely proportional to the intensity of the detection signal and directly proportional to the intensity of the calibration signal.

The present invention may be better understood with reference to the following examples.

EXAMPLE 1

The ability of various polyelectrolytes to be effectively utilized in an internal calibration zone of a half-dipstick sandwich assay was demonstrated. Initially, Millipore SX porous membrane samples made of nitrocellulose were laminated onto corresponding supporting cards having a length of approximately 30 centimeters. A variety of polyelectrolyte solutions were then stripped onto the membrane samples. The polyelectrolyte solutions were stripped on the membrane samples manually, with a plastic pipette tip, or through the use of a stripping machine. After application of the polyelectrolytes, the membranes were dried for 1 hour at a temperature of 37° C.

The following polyelectrolyte solutions were tested:

| Polyelectrolyte | Net Charge | Vendor | Brand | Concentration Ranges Tested (wt. %) |
|---|---|---|---|---|
| Polylysine | Positive | Sigma-Aldrich | Sigma | 2-25 |
| Polyethylenimine | Positive | Sigma-Aldrich | Aldrich | 2-25 |
| Poly(dimethylamine-co-epichlorohydrine) | Positive | Sigma-Aldrich | Aldrich | 2-25 |
| Polydiallyldimethyl ammonium chloride | Positive | Sigma-Aldrich | Aldrich | 2-25 |
| Poly(isoprene-b-N-methyl 2-vinyl pyridinium iodide | Amphiphilic | Polymer Source | N/A | 2-25 |
| Poly(ethylene-co-methacrylic acid, Na+), | Negative | Sigma-Aldrich | Aldrich | 2-25 |

The laminated membrane was then cut into small half dipsticks. A cellulosic fiber wicking pad (Millipore Co.) was attached to one end of the half dipstick. The other end of the membrane was inserted into a variety of probe suspensions. In particular, the following probes were tested:

| Probe | Color | Particle Size (microns) | Net Charge | Vendor |
|---|---|---|---|---|
| Colored Carboxylate Latex Beads | Blue | 0.3 | Positive | Bang's Laboratory, Inc. |

-continued

| Probe | Color | Particle Size (microns) | Net Charge | Vendor |
|---|---|---|---|---|
| Fluorescent Carboxylate Latex Beads | Red Green Yellow | 0.2 0.5 1.0 | Positive | Molecular Probes, Inc. |
| Acid Red 37 | Red | N/A | Positive | Sigma-Aldrich |

The half dipsticks were also inserted into suspensions of probe conjugates. In particular, the above-mentioned probes were conjugated with anti-C-reactive protein monoclonal antibody (anti-CRP Mab), anti-leutinizing hormone monoclonal antibody (anti-LH Mab), and anti-prealbumin polyclonal antibody (anti-Pab) using well-known techniques. For instance, a 100-microliter suspension of the 0.5-micron fluorescent carboxylated microspheres (available from Molecular Probes, Inc.) was initially washed two times with a phosphate buffer saline (PBS) and then re-suspended in 200 microliters of PBS. To the suspension, 5 mg carbodiimide was added and the mixture was mixed gently for 1 hour. The microspheres were then washed twice with a borate buffer and then washed. The microspheres were re-suspended in a 185-microliter borate buffer. 15 microliters of α-LH monoclonal antibody (9.7 mg/ml) were then added to the suspension and allowed to react for 3 hours under gentle mixing. Thereafter, 200 microliters of a 1M ethanolamine aqueous solution were added to the reaction mixture for 20 minutes. The microspheres were then washed two times using PBS and stored in PBS.

The probe and probe conjugate suspensions contained water and 1.6% polyoxyethylene sorbitan monolaurate (a nonionic surfactant available from Sigma-Aldrich under the name "Tween 20"). The resulting concentration of the probes ranged from 0.001-5 mg/ml and the concentration of the probe conjugates range from 0.2-10 mg/ml. After about 10 minutes, the stripped calibration line of each sample was then observed to determine if the probes/probes conjugates were visually detectable.

The polylysine, polyethylenimine, poly(dimethylamine-co-epichlorohydrine) and polydiallyidimethyl-ammonium chloride exhibit almost complete capturing of the above probes and their conjugates on the porous membrane when their capturing capacities are larger than the amount of probes and probe conjugates. Among the polyelectrolytes above, polylysine and polyethylenimine performed the best in terms of capturing efficiency (little of the probes or probe conjugates overran the calibration line when the amount of probes or probe conjugates was less than the total capacity); line quality (sharp line and clear edge); and diffusion (sharp lines remained after 30 minutes).

In addition, the amphiphilic poly(isoprene-b-N-methyl 2-vinyl pyridinium iodide) was determined to readily capture charged probes and probe conjugates. Similarly, the negatively charged poly(ethylene-co-methacrylic acid, Na+) readily captured positively charged latex beads, such as the colored carboxylated, amine-terminated latex beads from Bang's Laboratory, Inc., and their conjugates. They were also found to form good control/calibration lines. Interestingly, some of the polyelectrolytes also captured probes or probe conjugates of the same charge. For examples, polyethylenimine captured both carboxylated and amino-terminated latex beads and their antibody conjugates on membranes to form control/calibration lines. However, the captured particles with the same net charge as the polyelectrolytes tended to exhibit greater diffusion through the membrane than the captured particles with the oppositely charged polyelectrolytes.

EXAMPLE 2

The ability to control the capturing capacity of polyethylenimine in an internal calibration zone of a half-dipstick sandwich assay was demonstrated. Initially, Millipore SX porous membrane samples made of nitrocellulose were laminated onto corresponding supporting cards having a length of approximately 30 centimeters. Aqueous solutions of polyethylenimine were then stripped onto the membrane with a plastic pipette tip at concentrations of 1.6%, 2%, and 7.4%. After application of the polyethylenimine, the membranes were dried for 1 hour at a temperature of 37° C.

The laminated membrane was then cut into small half dipsticks. A cellulosic fiber wicking pad (Millipore Co.) was attached to one end of the half dipstick. The other end of the membrane was inserted into a variety of probe and probe conjugate suspensions as described in Example 1. After being immersed in the applicable probe and/or probe conjugate suspension for approximately 10 minutes, the stripped calibration line of each sample was then observed to determine if the probes/probes conjugates were visually detectable.

Upon observation, it was determined that the calibration line formed by the 7.4% polyethylenimine solution exhibited a higher intensity than the calibration line formed by the 2% polyethylenimine solution when excess blue latex beads (0.3 μm, from Bang's Laboratory, Inc.) were applied. In addition, it was also determined that the calibration line formed by the 7.4% polyethylenimine solution exhibited a higher intensity than the calibration line formed by the 1.6% polyethylenimine solution when red fluorescent microspheres conjugated with anti-α-LH Mab was applied.

EXAMPLE 3

The ability of polyethylenimine to be effectively utilized in an internal calibration zone of a half-dipstick sandwich assay was demonstrated. Initially, Millipore SX porous membrane samples made of nitrocellulose were laminated onto corresponding supporting cards having a length of approximately 30 centimeters.

A 7.4% polyethylenimine aqueous solution was stripped onto the Millipore SX membrane to form a single calibration line and anti-C-reactive protein (anti-CRP) monoclonal antibody (Mab A5804, 1 mg/ml, obtained from BiosPacific, Inc.) was stripped onto the membrane to form a detection line. The membrane was dried for 1 hour at a temperature of 37° C. The laminated membrane was then cut into small half dipsticks. A cellulosic fiber wicking pad (Millipore Co.) was attached to one end of the half dipstick.

One of the half dipsticks was applied to a control well that contained Tween 20, anti-C-reactive protein (anti-CRP) Mab conjugated to blue latex beads (anti-CRP Mab-beads), and water, while the other half dipstick was applied to a test well that contained C-reactive protein (CRP), Tween 20, anti-CRP Mab conjugated to blue latex beads (anti-CRP Mab-beads), and water. The mixture in each well migrated along the corresponding half dipstick to the detection line, calibration line, and wicking pad of the dipstick.

For the dipstick applied with the mixture in the test well, the CRP analyte was captured by the anti-CRP Mab-beads at the detection line, while any remaining unbound anti-CRP Mab-beads were captured by the polyethylenimine solution at the calibration line. Thus, after about 10 minutes, blue lines were observed on both the detection line and the calibration line. Likewise, for the dipstick applied with the mixture in the control well, all of the anti-CRP Mab-beads were captured at the calibration line. As a result, a blue line was observed only on the calibration line.

EXAMPLE 4

The ability of polyethylenimine to be effectively utilized in an internal calibration zone of a full-dipstick sandwich assay was demonstrated. Initially, two Millipore SX porous membrane samples made of nitrocellulose were laminated onto corresponding supporting cards having a length of approximately 30 centimeters. A cellulosic fiber wicking pad (Millipore Co.) was attached to one end of the membranes, while a cellulosic fiber sample pad (Millipore Co.) was attached to the other end of the membranes. A glass fiber conjugate pad (Millipore Co.) was also disposed on the membranes adjacent to the sample pad.

A 7.4% polyethylenimine aqueous solution was stripped onto each Millipore SX membrane to form a single calibration line. The conjugate pads were loaded with anti-C-reactive protein (anti-CRP) monoclonal antibody (Mab A5804, 1 mg/ml, obtained from BiosPacific, Inc.) beads to form a detection line. The membranes were dried for 1 hour at a temperature of 37° C.

The sample pad of one dipstick was then applied to a control well that contained only phosphate buffer saline (PBS), while the sample pad of the other dipstick was applied to a test well that contained C-reactive protein (CRP), 1.6% Tween 20, and water. The mixture in each well migrated along the corresponding dipstick to the detection line, calibration line, and wicking pad of the dipstick.

For the dipstick applied with the mixture in the test well, the CRP analyte was captured by the anti-CRP Mab-beads at the detection line, while any remaining unbound anti-CRP Mab-beads were captured by the polyethylenimine solution at the calibration line. Thus, after about 10 minutes, blue lines were observed on both the detection line and the calibration line. Likewise, for the dipstick applied with the mixture in the control well, all of the anti-CRP Mab-beads were captured at the calibration line. As a result, a blue line was observed only on the calibration line.

EXAMPLE 5

The ability of polyethylenimine to be effectively utilized in an internal calibration zone of a half-dipstick sandwich assay was demonstrated. Initially, Millipore SX porous membrane samples made of nitrocellulose were laminated onto corresponding supporting cards having a length of approximately 30 centimeters.

A 7.4% polyethylenimine aqueous solution was stripped onto the Millipore SX membrane to form a single calibration line and anti-β-leutinizing hormone (anti-β-LH) monoclonal antibody (Mab, 1 mg/ml, obtained from Fitzgerald Industries Int'l, Inc.) was stripped onto the membrane to form a detection line. The membrane was dried for 1 hour at a temperature of 37° C. The laminated membrane was then cut into small half dipsticks. A cellulosic fiber wicking pad (Millipore Co.) was attached to one end of the half dipstick.

One of the half dipsticks was applied to a control well that contained Tween 20, anti-α-leutinizing hormone (anti-α-LH) Mab conjugated to blue latex beads (anti-α-LH Mab-beads), and water, while the other half dipstick was applied to a test well that contained β-leutinizing hormone (LH), Tween 20, anti-α-leutinizing hormone (anti-α-LH) Mab conjugated to blue latex beads (anti-α-LH Mab-beads), and water. The mixture in each well migrated along the corresponding half dipstick to the detection line, calibration line, and wicking pad of the dipstick.

For the dipstick applied with the mixture in the test well, the LH analyte bound with the anti-α-LH Mab-beads was then captured at the detection line by the anti-β-LH Mab, while any remaining unbound anti-α-LH Mab-beads were captured by the polyethylenimine solution at the calibration line. Thus, after about 10 minutes, blue lines were observed on both the detection line and the calibration line. Likewise, for the dipstick applied with the mixture in the control well, all of the anti-α-LH Mab-beads were captured at the calibration line. As a result, a blue line was observed only on the calibration line.

EXAMPLE 6

The ability of polyethylenimine to be effectively utilized in an internal calibration zone of a half-dipstick sandwich assay was demonstrated. Initially, a HF10220 obtained from Millipore Co. porous membrane samples made of nitrocellulose were laminated onto corresponding supporting cards having a length of approximately 30 centimeters.

A 7.4% polyethylenimine aqueous solution was stripped onto the membrane to form a single calibration line and pre-albumin (1 mg/ml, obtained from Biogenesis, Inc.) was stripped onto the membrane to form a detection line. The membrane was dried for 1 hour at a temperature of 37° C. The laminated membrane was then cut into small half dipsticks. A cellulosic fiber wicking pad (Millipore Co.) was attached to one end of the half dipstick.

One of the half dipsticks was applied to a control well that contained 10 μl red fluorescent microspheres conjugated with anti-prealbumin polyclonal antibody, while the other half dipstick was applied to a test well that contained 20 microliters of pre-albumin (0.2 mg/ml in phosphate buffer saline), 10 microliters of red fluorescent microspheres conjugated with anti-prealbumin polyclonal antibody and 40 microliters of 2% Tween 20 aqueous solution. The mixture in each well migrated along the corresponding half dipstick to the detection line, calibration line, and wicking pad of the dipstick.

For the dipstick applied with the mixture in the test well, the pre-albumin analyte was captured by the anti-prealbumin polyclonal antibody beads. The prealbumin bound beads passed the detection line and were captured on the calibration line. Thus, after about 10 minutes, red lines were observed only on the calibration line. Likewise, for the dipstick applied with the mixture in the control well, the anti-prealbumin polyclonal antibody beads were captured first on the detection line, and then some of the remaining beads were captured on the calibration line. As a result, red lines were observed on the detection and calibration lines.

EXAMPLE 7

The ability of an internal calibration zone of the present invention to calibrate a sandwich assay was demonstrated. Initially, Millipore SX porous membrane samples made of nitrocellulose were laminated onto corresponding supporting cards having a length of approximately 30 centimeters. Aqueous solutions of polyethylenimine were then stripped onto the membrane (1×, 10×, and 100× dilution of 7.4% polyethyleneimine solution) to form three separate calibration lines of different concentrations. After application of the polyethylenimine, the membranes were dried for 1 hour at a temperature of 37° C.

A cellulosic fiber wicking pad (Millipore Co.) was attached to one end of the membrane. The other end of the membrane was inserted into a variety of probe and probe conjugate suspensions. In particular, the following probes were tested:

| Probe | Color | Particle Size (microns) | Net Charge | Vendor |
|---|---|---|---|---|
| Colored Carboxylate Latex Beads | Blue | 0.3 | Positive | Bang's Laboratory, Inc. |
| Fluorescent Carboxylate Latex Beads | Red | 0.5 | Positive | Molecular Probes, Inc. |

The assays were also inserted into suspensions of probe conjugates. In particular, the above-mentioned probes were conjugated with anti-C-reactive protein monoclonal antibody (anti-CRP Mab), anti-leutinizing hormone monoclonal antibody (anti-LH Mab), and anti-prealbumin polyclonal antibody (anti-Pab) using well-known techniques. For instance, a 100-microliter suspension of the 0.5-micron fluorescent carboxylated microspheres (available from Molecular Probes, Inc.) was initially washed two times with a phosphate buffer saline (PBS) and then re-suspended in 200 microliters of PBS. To the suspension, 5 mg carbodiimide was added and the mixture was mixed gently for 1 hour. The microspheres were then washed twice with a borate buffer and then washed. The microspheres were re-suspended in a 185-microliter borate buffer. 15 microliters of α-LH monoclonal antibody (9.7 mg/ml) were then added to the suspension and allowed to react for 3 hours under gentle mixing. Thereafter, 200 microliters of a 1M ethanolamine aqueous solution were added to the reaction mixture for 20 minutes. The microspheres were then washed two times using PBS and stored in PBS.

The probe and probe conjugate suspensions contained water and 1.6% polyoxyethylene sorbitan monolaurate (a nonionic surfactant available from Sigma-Aldrich under the name "Tween 20"). The resulting concentration of the probes ranged from 0.001-5 mg/ml and the concentration of the probe conjugates range from 0.2-10 mg/ml.

After about 5 minutes, the stripped calibration lines were then observed to determine if the probes/probes conjugates were visually detectable. The line containing the 1× diluted solution exhibited the highest signal intensity, while the line containing the 100× diluted exhibited the lowest signal intensity.

EXAMPLE 8

The ability of an internal calibration zone of the present invention to calibrate a half-dipstick sandwich assay was demonstrated. Initially, Millipore SX porous membrane samples made of nitrocellulose were laminated onto corresponding supporting cards having a length of approximately 30 centimeters. 7.4% polyethylenimine aqueous solutions (1×, 100×, and 100× diluted samples) were then stripped onto the Millipore SX membrane to form three calibration lines of different concentrations.

Anti-C-reactive protein (anti-CRP) monoclonal antibody (Mab A5804, 1 mg/ml, obtained from BiosPacific, Inc.) was stripped onto the membrane to form a detection line. The membrane was dried for 1 hour at a temperature of 37° C. A cellulosic fiber wicking pad (Millipore Co.) was attached to one end of the membrane. The laminated membrane was then cut into small half dipsticks.

The end of the membrane opposite to the wicking pad was applied to a test well that contained C-reactive protein (CRP), Tween 20, anti-CRP Mab conjugated to blue latex beads (anti-CRP Mab-beads), and water. The mixture in the well migrated along the half dipstick to the detection line, calibration lines, and wicking pad of the dipstick.

The CRP analyte was captured by the anti-CRP Mab-beads at the detection line, while any remaining unbound anti-CRP Mab-beads were captured by the calibration lines. Thus, after about 5 minutes, one blue line was observed on the detection line, while three blue lines were observed on the calibration lines. The line containing the 1× diluted solution exhibited the highest signal intensity, while the line containing the 100× diluted exhibited the lowest signal intensity.

EXAMPLE 9

The ability of an internal calibration zone of the present invention to calibrate a half-dipstick sandwich assay was demonstrated. Initially, HF 09002 porous membrane samples made of nitrocellulose were laminated onto corresponding supporting cards having a length of approximately 30 centimeters. 0.14% (calibration #1), 0.64% (calibration #2), and 1.4% (calibration #3) polyethylenimine aqueous solutions (1×, 10×, and 100× diluted samples) were then stripped onto the membrane to form three calibration lines of different concentrations.

Anti-C-reactive protein (anti-CRP) monoclonal antibody (Mab A5804, 1 mg/ml, obtained from BiosPacific, Inc.) was stripped onto the membrane to form a detection line. The membrane was dried for 1 hour at a temperature of 37° C. A cellulosic fiber wicking pad (Millipore Co.) was attached to one end of the membrane. The laminated membrane was then cut into small half dipsticks.

The end of the membrane opposite to the wicking pad was applied to three test wells that contained Tween 20, an excess amount of anti-CRP Mab conjugated to blue latex beads (anti-CRP Mab-beads), and water. The test wells also contained different concentrations of C-reactive protein (CRP). In particular, the solutions contained 0 nanograms (ng), 0.54 ng, 5.4 ng, and 54 ng of CRP, respectively.

The mixture in the wells migrated along each half dipstick to the detection line, calibration lines, and wicking pad of the dipstick. The CRP analyte was captured by the anti-CRP Mab-beads at the detection line, while any remaining unbound anti-CRP Mab-beads were captured by the calibration lines. Thus, for each sample, one blue line was observed on the detection line, while three blue lines were observed on the calibration lines. The line containing the 1.4% polyethyleneimine solution exhibited the highest signal intensity, while the line containing the 0.14% polyethyleneimine solution exhibited the lowest signal intensity. Based on analysis, it was determined that calibration line #1 contained 0.54 ng of CRP, calibration line #2 contained 5.4 ng of CRP, and calibration line #3 contained 54 ng of CRP.

Thus, when an unknown test sample is tested, CRP concentration can be visually determined by comparing the detection line with the three calibration lines. In particular, when the detection line intensity is visually determined to have an intensity between the intensity of calibration lines #2 and #3, the CRP concentration is between 5.4 and 54 ng. Likewise, when the detection line intensity is visually determined to have an intensity between the intensity of calibration lines #1 and #2, the CRP concentration is between 0.54 and 5.4 ng. Further, a detection line having an intensity less than the intensity of the calibration line #1 has a CRP concentration less than 0.54 ng, while a detection line having an intensity greater than the intensity of the calibration line #3 has a CRP concentration greater than 54 ng.

Figure 6:
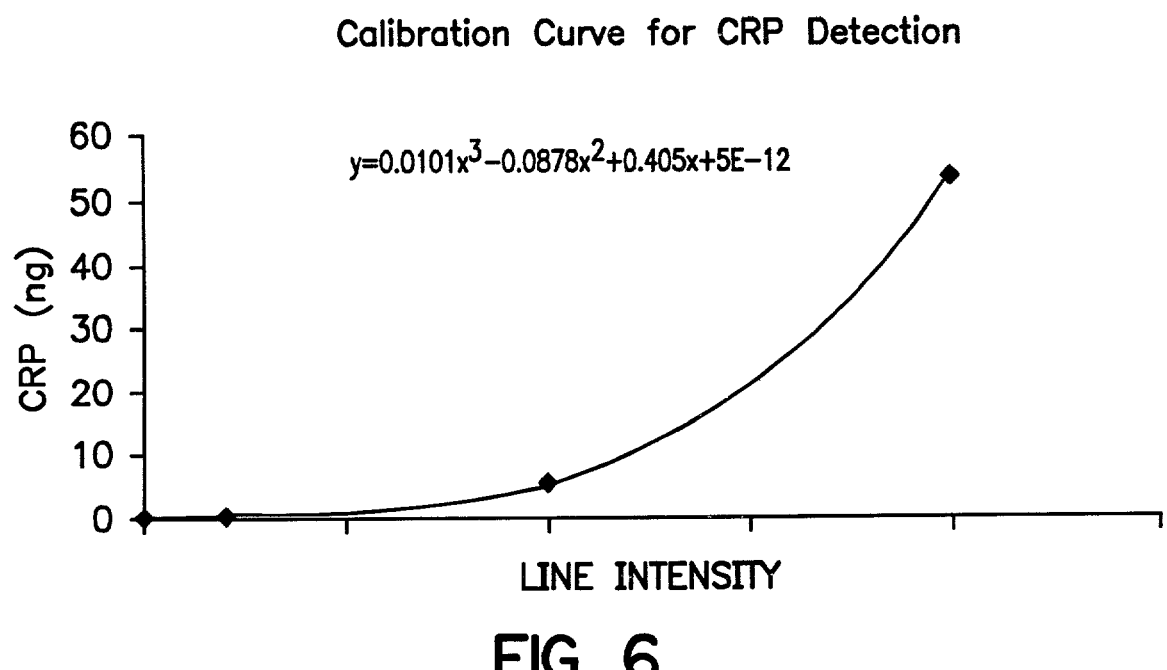
FIG. 6 shows a calibration curve for CRP detection as discussed in Example 9.

The calibration line intensity can also be measured by an instrument, such as an assay reader. For example, a calibration curve (shown in FIG. 6) was developed using the line intensities of calibration lines #1-#3 and their CRP concentrations. The mathematical equation generated by the calibration curve can be inputted into an instrument that is able to read intensity for detection of CRP in a test sample.

EXAMPLE 10

The ability of an internal calibration zone of the present invention to calibrate a half-dipstick sandwich assay was demonstrated. Initially, SHF 075 porous membrane samples made of nitrocellulose were laminated onto corresponding supporting cards having a length of approximately 30 centimeters. Varying concentrations of CelQuat® H-100 (a cellulosic derivative available from National Starch & Chemical, Inc.) were stripped onto the membrane to form three calibration lines having different concentrations. In particular, the concentrations utilized were 2.5 parts CelQuat® H-100 per million of the solution (ppm) (calibration #1), 5 ppm (calibration #2), and 20 ppm (calibration #3).

Anti-β-utilizing hormone (anti-β-LH) monoclonal antibody (Mab, 1 mg/ml, obtained from Fitzgerald Industries Intl., Inc.) was stripped onto the membrane to form a detection line. The membrane was dried for 1 hour at a temperature of 37° C. A cellulosic fiber wicking pad (Millipore Co.) was attached to one end of the membrane. The laminated membrane was then cut into small half dipsticks.

The end of the membrane opposite to the wicking pad was applied to a test well that contained Tween 20, anti-α-leutinizing hormone (anti-α-LH) Mab conjugated to blue latex beads (anti-α-LH Mab-beads), and water. The mixture also contained varying concentrations of β-leutinizing hormone (LH). In particular, the concentrations tested were 0 ppm, 20 ppm, and 100 ppm, which corresponded to solutions containing 0 nanograms (ng), 20 ng, and 100 ng of LH, respectively.

The mixture in the wells migrated along each half dipstick to the detection line, calibration lines, and wicking pad of the dipstick. The LH analyte was captured by the anti-α-LH Mab-beads at the detection line, while any remaining unbound anti-α-LH Mab-beads were captured by the calibration lines. Thus, for each sample, one blue line was observed on the detection line, while three blue lines were observed on the calibration lines. The line containing the 20 ppm CelQuat® solution exhibited the highest signal intensity, while the line containing the 2.5 ppm CelQuat® solution exhibited the lowest signal intensity. Based on analysis, it was determined that calibration line #1 contained 20 ng of LH and calibration line #3 contained 100 ng of LH. Moreover, using an instrument capable of reading line intensity, it was determined that calibration lines #1, #2, and #3 had a line intensity of 1, 2, and 4, respectively.

Figure 7:
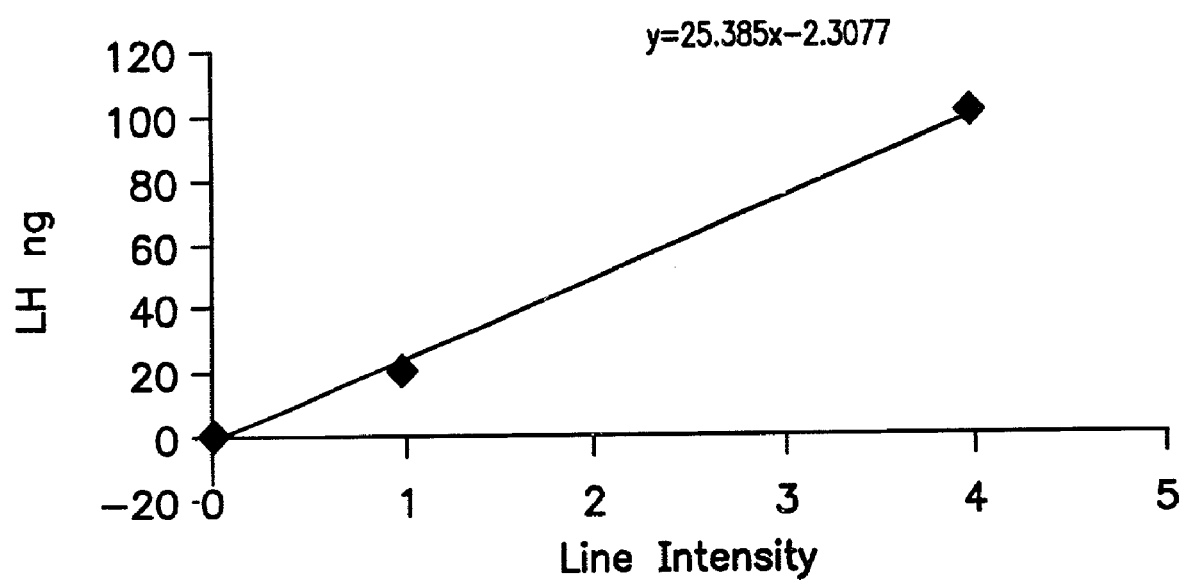
FIG. 7 shows a calibration curve for LH detection as discussed in Example 10.

A calibration curve (shown in FIG. 7) was then developed using the line intensities of calibration lines #1-#3 and their LH concentrations. The mathematical equation generated by the calibration curve was then inputted into an instrument. A test sample containing an unknown level of LH was then applied to a membrane formed as described above. Using the instrument, it was determined that the intensity of the detection signal was about 1.5. As a result, it was determined that the concentration of the LH in the unknown test sample was about 36 ng.

EXAMPLE 11

The ability of an internal calibration zone of the present invention to calibrate a half-dipstick competitive assay was demonstrated. Initially, HF 120 porous membrane samples made of nitrocellulose were laminated onto corresponding supporting cards having a length of approximately 30 centimeters. Varying concentrations of CelQuat® H-100 (a cellulosic derivative available from National Starch & Chemical, Inc.) were stripped onto the membrane to form three calibration lines having different concentrations. In particular, the concentrations utilized were 2.5 parts CelQuat® H-100 per million of the solution (ppm) (calibration #1), 5 ppm (calibration #2), and 20 ppm (calibration #3).

Pre-albumin (1 mg/ml, obtained from Biogenesis, Inc.) was stripped onto the membrane to form a detection line. The membrane was dried for 1 hour at a temperature of 37° C. A cellulosic fiber wicking pad (Millipore Co.) was attached to one end of the membrane. The laminated membrane was then cut into small half dipsticks.

The end of the membrane opposite to the wicking pad was applied to a test well that contained 30 microliters of 2% Tween 20, 10 microliters of red fluorescent microspheres conjugated with anti-prealbumin polyclonal antibody, and water. The mixture also contained varying concentrations of pre-albumin in phosphate buffer saline. In particular, the concentrations tested were 0 micrograms, 75 micrograms, and 125 micrograms.

It was observed that the three calibration lines turned different intensities of red, where the calibration line #3 has the highest and line #1 has the lowest intensity. The intensity of the detection line in this competitive assay was inversely proportional to the test pre-albumin concentration. When there was no pre-albumin, the conjugate was captured by the detection line and the three calibration lines. With an increased amount of pre-albumin antigen, the detection line became less intense.

The line intensity was then read by a fluorescence reader and used to generate a calibration curve. The results are shown below in Table 1.

TABLE 1

Calibration for Pre-albumin Detection with Line Intensity

|  | Signal Intensity | | |
|---|---|---|---|
| Calibration #1 | 1 | 1 | 1 |
| Calibration #2 | 10 | 10 | 10 |
| Calibration #3 | 20 | 20 | 20 |
| Detection Line | 20 | 10 | 0 |

Figure 8:
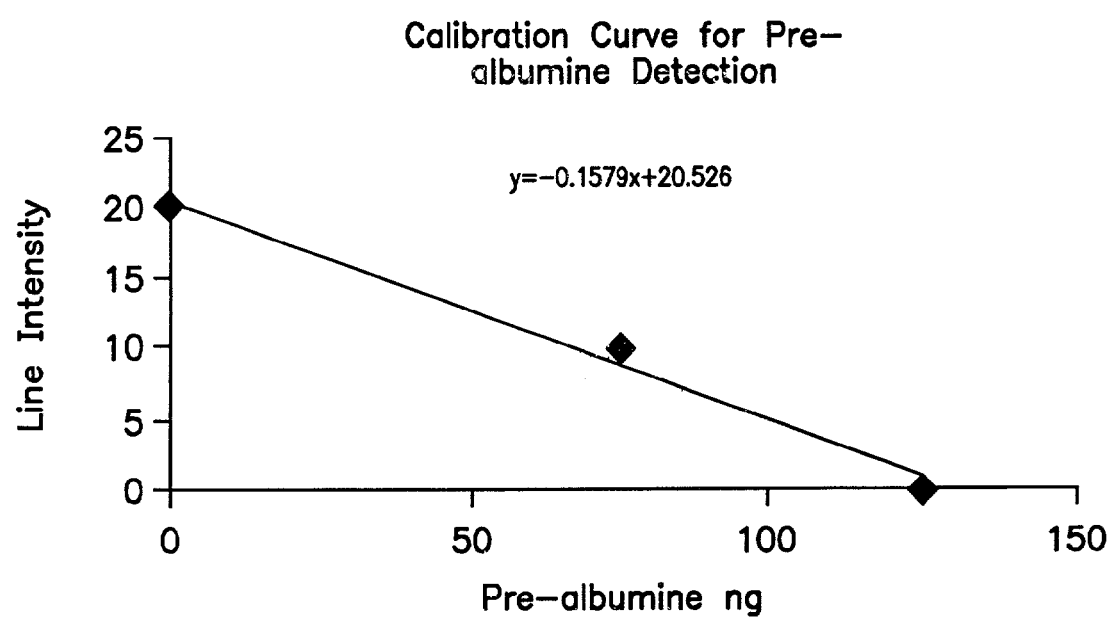
FIG. 8 shows a calibration curve for pre-albumin detection as discussed in Example 11.

For the detection line, the signal intensity values of 20, 10, and 0 was determined to correspond to pre-albumin amounts of 0 micrograms, 75 micrograms, and 125 micrograms, respectively. A calibration curve generated from this data is also shown in FIG. 8. Using this calibration curve, the presence and/or amount of an unknown level of pre-albumin can be determined.

While the invention has been described in detail with respect to the specific embodiments thereof, it will be appreciated that those skilled in the art, upon attaining an understanding of the foregoing, may readily conceive of alterations to, variations of, and equivalents to these embodiments. Accordingly, the scope of the present invention should be assessed as that of the appended claims and any equivalents thereto.

What is claimed is:

1. A flow-through assay device for detecting an analyte within a test sample, the flow-through assay device comprising a porous membrane in fluid communication with detectable probes conjugated with a specific binding member, the conjugated probes having a net charge prior to the application of a test sample to the device, the porous membrane defining:
    a detection zone that contains a capture reagent configured to bind with the conjugated probes or complexes thereof to generate a detection signal; and
    a calibration zone positioned downstream from the detection zone, wherein a polyelectrolyte is substantially non-diffusively immobilized on the porous membrane within the calibration zone, the polyelectrolyte having a net charge opposite to that of the conjugated probes, the polyelectrolyte being configured to bind with the conjugated probes to generate a calibration signal.

2. The flow-through assay device of claim 1, wherein the polyelectrolyte has a net positive charge.

3. The flow-through assay device of claim 1, wherein the calibration zone contains at least two distinct regions having a different concentration of the polyelectrolyte.

4. The flow-through assay device of claim 1, wherein the polyelectrolyte is ionically bonded to a functional group present on the surface of the porous membrane.

5. The flow-through assay device of claim 1, wherein the polyelectrolyte is covalently bonded to a functional group present on the surface of the porous membrane.

6. The flow-through assay device of claim 5, wherein the polyelectrolyte is crosslinked to the functional group.

7. The flow-through assay device of claim 1, wherein the detectable probes are selected from the group consisting of chromogens, catalysts, fluorescent compounds, chemiluminescent compounds, radioactive labels, direct visual labels, liposomes, and combinations thereof.

8. The flow-through assay device of claim 1, wherein the detectable probes comprise latex microparticles.

9. The flow-through assay device of claim 1, wherein the specific binding member is selected from the group consisting of antigens, haptens, antibodies, and complexes thereof.

10. The flow-through assay device of claim 1, wherein the capture reagent is selected from the group consisting of antigens, haptens, antibodies, and complexes thereof.

11. The flow-through assay device of claim 1, wherein the capture reagent is configured to bind with complexes formed between the conjugated probes and the analyte.

12. The flow-through assay device of claim 1, wherein the capture reagent is configured to bind with the specific binding member.

13. The flow-through assay device of claim 1, wherein the capture reagent is substantially non-diffusively immobilized on the porous membrane.

14. The flow-through assay device of claim 1, wherein the amount of the analyte within the test sample is quantitatively or semi-quantitatively determined by comparing the detection signal to the calibration signal.

15. The flow-through assay device of claim 1, wherein the calibration zone is generally free of biological capture reagents.

* * * * *

UNITED STATES PATENT AND TRADEMARK OFFICE
CERTIFICATE OF CORRECTION

PATENT NO. : 7,651,841 B2
APPLICATION NO. : 10/132421
DATED : January 26, 2010
INVENTOR(S) : Song et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1064 days.

Signed and Sealed this

Twenty-third Day of November, 2010

David J. Kappos
*Director of the United States Patent and Trademark Office*